United States Patent
Zhang et al.

(10) Patent No.: US 9,376,382 B2
(45) Date of Patent: Jun. 28, 2016

(54) N-SUBSTITUTED ISOPROPYLDIMETHYL AZULENE SULFONAMIDE DERIVATIVES, AND PREPARATION METHOD AND USE THEREOF

(75) Inventors: Luyun Zhang, Sichuan (CN); Fang Yang, Sichuan (CN); Wanqi Shi, Sichuan (CN); Ping Zhang, Sichuan (CN); Ying Li, Sichuan (CN); Shufan Yin, Sichuan (CN)

(73) Assignee: Sichuan Guokang Pharmaceutical Co., Ltd., Chengdu (CN)

(*) Notice: Subject to any disclaimer, the term of this patent is extended or adjusted under 35 U.S.C. 154(b) by 0 days.

(21) Appl. No.: 14/127,754

(22) PCT Filed: Apr. 12, 2012

(86) PCT No.: PCT/CN2012/073855
§ 371 (c)(1),
(2), (4) Date: Mar. 25, 2014

(87) PCT Pub. No.: WO2012/174926
PCT Pub. Date: Dec. 27, 2012

(65) Prior Publication Data
US 2014/0206741 A1    Jul. 24, 2014

(30) Foreign Application Priority Data

Jun. 20, 2011 (CN) .......................... 2011 1 0164799
Jun. 27, 2011 (CN) .......................... 2011 1 0175378

(51) Int. Cl.
| | |
|---|---|
| C07C 317/44 | (2006.01) |
| C07C 317/30 | (2006.01) |
| C07C 311/51 | (2006.01) |
| C07C 315/04 | (2006.01) |
| C07C 311/49 | (2006.01) |
| C07C 303/40 | (2006.01) |
| C07C 311/29 | (2006.01) |
| C07D 333/22 | (2006.01) |
| C07C 311/14 | (2006.01) |
| C07D 209/18 | (2006.01) |
| C07D 333/24 | (2006.01) |
| C07D 207/48 | (2006.01) |
| A61K 31/18 | (2006.01) |
| A01N 41/06 | (2006.01) |
| C07D 333/36 | (2006.01) |
| C07D 209/20 | (2006.01) |
| A61K 31/216 | (2006.01) |
| A61K 31/223 | (2006.01) |
| A61K 31/225 | (2006.01) |
| A61K 31/405 | (2006.01) |

(52) U.S. Cl.
CPC .............. *C07C 317/30* (2013.01); *A01N 41/06* (2013.01); *A61K 31/18* (2013.01); *A61K 31/216* (2013.01); *A61K 31/223* (2013.01); *A61K 31/225* (2013.01); *A61K 31/405* (2013.01); *C07C 303/40* (2013.01); *C07C 311/14* (2013.01); *C07C 311/29* (2013.01); *C07C 311/49* (2013.01); *C07C 311/51* (2013.01); *C07C 315/04* (2013.01); *C07C 317/44* (2013.01); *C07D 207/48* (2013.01); *C07D 209/18* (2013.01); *C07D 209/20* (2013.01); *C07D 333/22* (2013.01); *C07D 333/24* (2013.01); *C07D 333/36* (2013.01); *C07C 2101/14* (2013.01); *C07C 2102/30* (2013.01)

(58) Field of Classification Search
CPC .. C07D 209/42; C07D 209/20; C07D 401/12; C07D 209/12; C07D 333/10; A61K 31/405; A61K 31/18; C07C 317/30; C07C 315/04; C07C 311/14; C07C 311/50; C07C 317/44; C07C 303/40
USPC ........... 514/419, 562, 601; 548/495; 562/427; 564/80
See application file for complete search history.

(56) References Cited

FOREIGN PATENT DOCUMENTS

| | | | |
|---|---|---|---|
| CN | 102287929 | 12/2011 | |
| DE | 1227896 B | * 11/1966 | ............ C07C 311/02 |
| JP | 2002105044 | 4/2002 | |
| JP | 2002105044 A | * 4/2002 | |

OTHER PUBLICATIONS

Zhang, et al. "Synthesis and antigastric ulcer activity of novel 5-isoproyl-3,8-dimethylazulene derivatives", Bioorganic & Medicinal Chemistry Letters, 21 (19), Oct. 2011.
Yang, et al., "Synthesis and anti-gastric ulcer activity on novel N-substituted gualazulene-1-sulfonamides derivatives", Dec. 2011.

* cited by examiner

*Primary Examiner* — Alicia L Otton
*Assistant Examiner* — Sagar Patel
(74) *Attorney, Agent, or Firm* — Cesari and McKenna LLP

(57) ABSTRACT

The present invention provides an N-substituted isopropyldimethyl azulene sulfonamide derivative as represented by formula (I), and preparation method and uses thereof, wherein R1 is an alkyl, cycloalkyl, alkenyl, alkynyl, aryl, heteroaryl, amino, or a substituted alkyl, cycloalkyl, alkenyl, alkynyl, aryl, heteroaryl, and amino. The N-substituted isopropyldimethyl azulene sulfonamide derivative can be used in treating gastric ulcer.

(1)

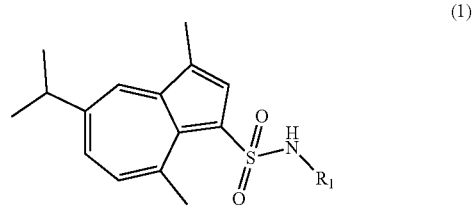

10 Claims, No Drawings

N-SUBSTITUTED ISOPROPYLDIMETHYL AZULENE SULFONAMIDE DERIVATIVES, AND PREPARATION METHOD AND USE THEREOF

FIELD OF THE INVENTION

The present invention relates to an N-substituted isopropyldimethyl azulene sulfonamide derivative, and preparation method and use thereof.

BACKGROUND OF THE INVENTION

Guaiazulene, namely 1,4-dimethyl-7-isoproylazulene, is an active ingredient of Chrysanthemum plants, which has a structural formula as follows:

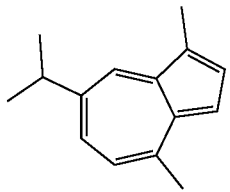

Guaiazulene has strong effect of anti pepsin, anti-inflammatory, anti-allergic and promoting mucosal metabolism. Its many derivatives also exhibit excellent biological activity. Compound Guaiazulene Ointment (Shanxi Tongsheng Pharmaceutical Co., Ltd.) can be used for burns, scalds, scorches, frostbite, chap, decubitus, radiation heat, dermatitis and etc.

Since the excellent pharmacological activities of guaiazulene, there have been many studies on structural modification of Guaiazulene. The resultant derivatives include azulene sodium sulphonate, 3-(2-substituted thiazole-4-yl) guaiazulene, 1-(2-benzofuran acyl) guaiazulene and etc. Among which, azulene sodium sulphonate is a water-soluble derivative of guaiazulene, has excellent anti-inflammatory and wound healing properties, and is used as the main ingredient of the currently available drug Glutamine Granules for treating gastric ulcer. Azulene sodium sulphonate can directly act on the inflammatory mucosa and has better therapeutic effect on various gastritis, as well as complications of gastritis and ulcers.

However, it is found by experiments that azulene sodium sulphonate has some stability issues, especially poor light stability and heat stability. In order to ensure the safety of products, the cost of product storage and transportation must be increased to prevent decomposition of the active ingredient and generation of impurities, leading to increased production costs.

Currently, there is no report about structural modification to improve the stability of azulene sodium sulphonate.

SUMMARY OF THE INVENTION

The object of the present invention is to provide an N-substituted isopropyldimethyl azulene sulfonamide derivative with excellent stability, and preparation method and use thereof.

The present invention provides an N-substituted isopropyldimethyl azulene sulfonamide derivative as represented by formula (I), having a structural formula as follows:

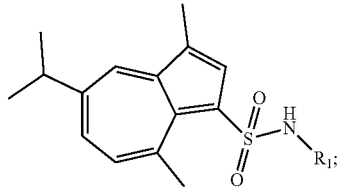

(1)

wherein $R_1$ is an alkyl, cycloalkyl, alkenyl, alkynyl, aryl, heteroaryl, amino, or a substituted alkyl, cycloalkyl, alkenyl, alkynyl, aryl, heteroaryl, and amino.

Further, $R_1$ is 3-$BrC_6H_4$, 2,4-$OCH_3C_6H_3$, iso-$C_3H_7$, 1-naphthyl, iso-$C_4H_9$, n-$C_3H_7$, 4-$CH_3C_6H_4$, $C_2H_5$, cyclohexyl, $CH_2C_6H_5$, 4-$ClC_6H_4$, 4-$NH_2C_6H_4$ or $NH_2$.

Wherein, the derivative has a structural formula as follows:

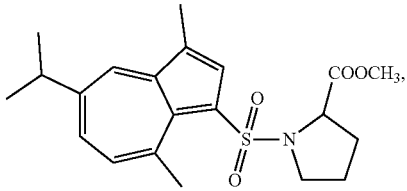

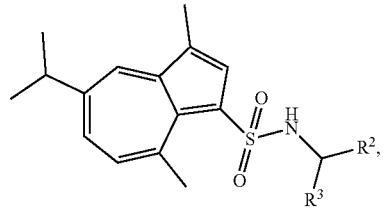

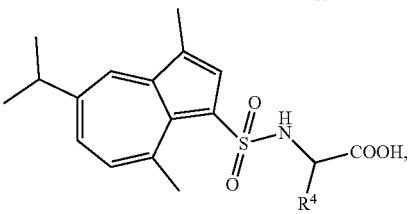

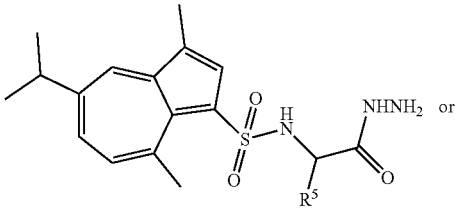

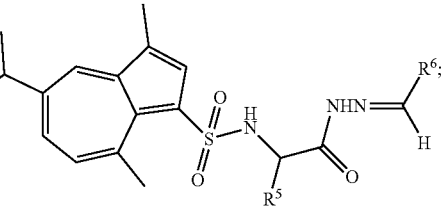

$R_2$ is hydrogen or methoxyformyl; $R_3$ is hydrogen, 2-methylpropyl, benzyl, indol-3-methyl, methyl, or methoxyformylmethyl; $R_4$ is hydrogen, 2-methylpropyl, or indol-3-methyl; $R_5$ is hydrogen or indol-3-methyl; $R_6$ is 2-thienyl or 4-trifluoromethylphenyl.

Further, the derivative is selected from the group consisting of:
N-2-(indol-3-methyl)-2-methoxyformylmethylene-3',8'-dimethyl-5'-isopropyl azulene-1'-sulfonamide;
N-3-methoxyformylethyl-3',8'-dimethyl-5'-isopropyl azulene-1'-sulfonamide;
N-2-(2-methylpropyl)-2-carboxymethylene-3',8'-dimethyl-5'-isopropyl azulene-1'-sulfonamide;
N-2-(indol-3-methyl)-2-carboxymethylene-3',8'-dimethyl-5'-isopropyl azulene-1'-sulfonamide, or
N-(2-carbonyl-2-(2-(2-thienylmethylene)ethyl)-3',8'-dimethyl-5'-isopropyl azulene-1'-sulfonamide.
Wherein,
$R_1$ is

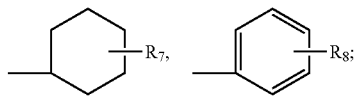

wherein, $R_7$, $R_8$ represent mono- or multi-substituted groups, which are selected from the group consisting of hydrogen, hydroxy, carboxy, halogen, $C_{1-4}$ alkoxyl, $C_{1-4}$ alkyl, amino and aryl group.
Further, $R_2$ is hydrogen, $R_3$ is selected from the group consisting of hydrogen, halogen, $C_{1-4}$ alkoxyl, $C_{1-4}$ alkyl, amino and aryl group, or $R_3$ together with a phenyl group which it is attached from an aromatic group.
Wherein, the halogen is Br.
Wherein, aryl represents a $C_{1-10}$ aromatic compound; $R_3$ together with a phenyl group which it is attached from a $C_{1-10}$ aromatic compound.
Further, the derivative is selected from the group consisting of:
N-(3-bromophenyl)-3,8-dimethyl-5-isopropyl-1-azulene sulfonamide;
N-(2,4-dimethoxyphenyl)-3,8-dimethyl-5-isopropyl-1-azulene sulfonamide;
N,5-diisopropyl-3,8-dimethyl-1-azulene sulfonamide;
N-(1-naphthyl)-3,8-dimethyl-5-isopropyl-1-azulene sulfonamide;
N-isobutyl-3,8-dimethyl-5-isopropyl-1-azulene sulfonamide;
N-propyl-3,8-dimethyl-5-isopropyl-1-azulene sulfonamide;
N-(4-methylphenyl)-3,8-dimethyl-5-isopropyl-1-azulene sulfonamide;
N-ethyl-3,8-dimethyl-5-isopropyl-1-azulene sulfonamide;
N-cyclohexyl-3,8-dimethyl-5-isopropyl-1-azulene sulfonamide;
N-benzyl-3,8-dimethyl-5-isopropyl-1-azulene sulfonamide;
N-(4-chlorophenyl)-3,8-dimethyl-5-isopropyl-1-azulene sulfonamide;
N-amino-3,8-dimethyl-5-isopropyl-1-azulene sulfonamide; or
N-(4-aminophenyl)-3,8-dimethyl-5-isopropyl-1-azulene sulfonamide.
More further, said derivative is selected from the group consisting of:
N-(3-bromophenyl)-3,8-dimethyl-5-isopropyl-1-azulene sulfonamide,
N-(2,4-dimethoxyphenyl)-3,8-dimethyl-5-isopropyl-1-azulene sulfonamide,
N-(1-naphthyl)-3,8-dimethyl-5-isopropyl-1-azulene sulfonamide,
N-cyclohexyl-3,8-dimethyl-5-isopropyl-1-azulene sulfonamide, or
N-(4-aminophenyl)-3,8-dimethyl-5-isopropyl-1-azulene sulfonamide.
More preferably, the derivative is N-(4-aminophenyl)-3,8-dimethyl-5-isopropyl-1-azulene sulfonamide.
The present invention provides a preparation method of the N-substituted isopropyldimethyl azulene sulfonamide derivative, comprising the following steps of:
subjecting azulene sodium sulphonate to acetyl chlorination to generate azulene sulfonyl chloride, reacting the azulene sulfonyl chloride with an amine compound to obtain said derivative; azulene sodium sulphonate is 1,4-dimethyl-7-isopropylazulene-3-sodium sulfonate.
Wherein, said amine compound is selected from the groups consisting of an aliphatic amine and aromatic amine.
Further, it comprises the following steps of:
adding azulene sodium sulphonate under ice bath with $CH_2Cl_2$, then adding with DMF and pyridine; adding a small amount of $CH_2Cl_2$, and then $(COCl)_2$, after completion of the reaction, slowly adding with a mixture solution of $Et_3N$, pyridine and an amine compound, reacting at room temperature followed by separating and purifying, to obtain said derivative.
According to the present invention, the preparation method of the N-substituted isopropyldimethyl azulene sulfonamide derivative comprises: reacting guaiazulene and acetic anhydride and concentrated sulfuric acid at room temperature and neutralizing with NaOH to generate azulene sodium sulphonate, then reacting the resultant azulene sodium sulphonate with chloroglyoxylate in the presence of pyridine and DMF to generate azulene sulfonyl chloride, reacting azulene sulfonyl chloride with amine in the presence of weak base to obtain the derivative of guaiazulene, N-substituted-5-isopropyl-3,8-dimethyl azulene sulfonamide, the reaction route of which is as follows:

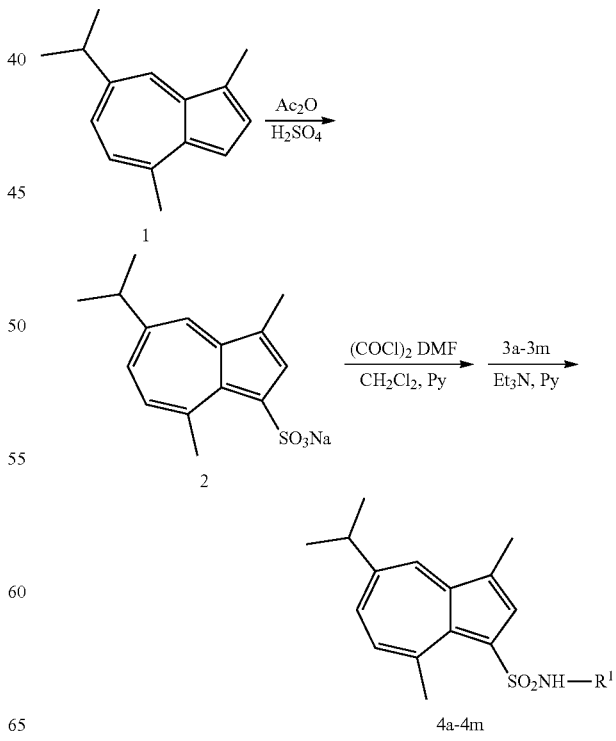

More further, it comprises the following steps:

(1) weighing raw materials according to the following ratios:

the molar ratio of azulene and oxalyl chloride being 1:2.5-3, the molar ratio of azulene and amine compound being 1:1.5-2;

(2) adding azulene sodium sulphonate under ice bath with $CH_2Cl_2$, then adding 3-5d DMF, adding pyridine; dropwise adding a small amount of $CH_2Cl_2$ and $(COCl)_2$; after completion of the reaction, adding a mixture solution of 2 ml of $Et_3N$, 1 ml of pyridine and an amine compound into the reaction solution; after completion of the dropwise addition, reacting the mixture at room temperature for 1 h, adding with an equal volume of water into the reaction flask, adjusting pH to 5-6 with dilute hydrochloric acid, extracting with $CH_2Cl_2$, and drying organic layer over anhydrous $Na_2SO_4$, removing the solvent by rotary evaporation, and purifying the crude product through column chromatography to obtain said derivative.

wherein, said aliphatic amine is one selected from the group consisting of isopropyl amine, isobutylamine, propylamine, ethylamine, cyclohexylamine and hydrazine hydrate; said aromatic amine is one selected from the group consisting of bromoaniline, 2,4-dimethoxy aniline, naphthylamine, toluidine, benzylamine, p-chloroaniline, and p-phenylenediamine.

The present invention also provides use of the N-substituted isopropyl dimethyl azulene sulfonamide derivative for preparing an anti digestive ulcer medicine.

Further, said medicine is an anti gastric ulcer medicine.

More further, said medicine is a medicine for treating alcohol-induced gastric ulcer.

The present invention also provides a pharmaceutical composition, which is a formulation that is prepared by one or a combination of two or more N-substituted isopropyldimethyl azulene sulfonamide derivatives as active ingredients, together with a pharmaceutically acceptable excipient or auxiliary component.

Wherein, said formulation is an oral or injectable formulation.

Further, said formulation is selected from the group consisting of tablets, pills, granules, capsules, powders, drop pills, and oral liquid.

The experiments demonstrate that N-(3-bromophenyl)-3,8-dimethyl-5-isopropyl-1-azulene sulfonamide (4a), N-(2,4-dimethoxyphenyl)-3,8-dimethyl-5-isopropyl-1-azulene sulfonamide (4b), N-(1-naphthyl)-3,8-dimethyl-5-isopropyl-1-azulene sulfonamide (4d), N-cyclohexyl-3,8-dimethyl-5-isopropyl-1-azulene sulfonamide (4i), N-(4-aminophenyl)-3,8-dimethyl-5-isopropyl-1-azulene sulfonamide (4l) provided by the present invention, can significantly relieve the pathological degree of anhydrous ethanol-induced gastric ulcer in mice, the ulcer scores of which have significant difference compared to the model group, and can be used as active pharmaceutical ingredients to develop new drugs of anti gastric ulcer with better therapeutic effect.

The N-substituted isopropyldimethyl azulene sulfonamide derivatives prepared according to the present invention not only improve the stability of azulene sodium sulphonate and retain the therapeutic effect of azulene sodium sulphonate on gastric ulcer disease, but also enhance the activity of azulene sodium sulphonate and have excellent social and economic values. Meanwhile, the preparation method of the derivatives is very simple and low-cost, and is suitable for industrialization and large scale production.

Clearly, many other modifications, replacements and changes can be made according to ordinary technical knowledge and conventional technical means based on the above disclosure, without departing from the basic technical idea of the present invention.

The above disclosure of the present invention will be illustrated in detail through the following examples as embodiments. However it should not be construed as limiting the invention to the examples shown below. The techniques achieved based on the above disclosure are within the scope of the present invention.

DETAILED DESCRIPTION OF THE INVENTION

Example 1

Preparation of N-(3-bromophenyl)-3,8-dimethyl-5-isopropyl-1-azulene sulfonamide (4a)

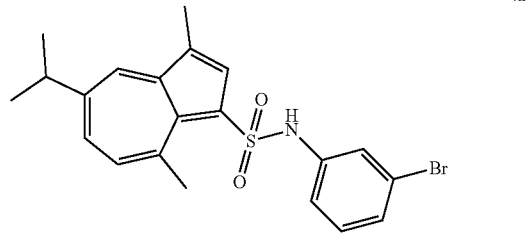

4a

The process steps of this example are as follows:

25 ml round-bottom flask was added with azulene sodium sulphonate (1 mmol), and then under ice bath added with 10 ml of $CH_2Cl_2$, 3-5 drops of DMF and 0.5 ml of pyridine. A dropping funnel was added with a small amount of $CH_2Cl_2$ and then added with $(COCl)_2$ (2.5 mmol), which was then slowly dropwise added into the round-bottom flask. After completion of the reaction, a mixture solution of 2 ml of $Et_3N$, 1 ml of pyridine and 3-bromoaniline (1.5 mmol) was slowly dropwise added into the reaction solution through a dropping funnel. After completion of dropwise addition, the mixture was reacted at room temperature for 1 h, and then added with an equal volume of water into the flask, and added with dilute hydrochloric acid to adjust pH to 5-6, extracted with $CH_2Cl_2$, and the organic layer was dried over anhydrous $Na_2SO_4$, then concentrated by rotary evaporation, and the resultant crude product was purified through column chromatography to obtain N-(3-bromophenyl)-3,8-dimethyl-5-isopropyl-1-azulene sulfonamide (purple crystals). Yield: 25%. m.p. 172-174° C. $^1$H NMR (400 MHz, $CDCl_3$) δ (ppm): 1.37 (d, J=7.2 Hz, 6H), 2.54 (s, 3H), 3.12 (q, J=7.2 Hz, J=7.2 Hz, 1H), 3.38 (s, 3H), 6.99 (d, J=8.0 Hz, 1H, PhH), 7.06 (t, J=8.0 Hz, 1H, PhH), 7.13 (d, J=8.0 Hz, 1H, PhH), 7.21 (s, 1H, PhH), 7.42 (d, J=10.4 Hz, 1H), 7.61 (d, J=11.2 Hz, 1H), 8.06 (s, 1H), 8.28 (d, J=2.0 Hz, 1H); IR (KBr) v: 3236, 2958, 2864, 1592, 1579, 1473, 1368, 1143, 775, 678, 587; HRMS (ESI) m/z calcd for $C_{21}H_{22}BrNO_2S$ [M+H]$^+$ 432.0627. found 432.0622.

Example 2

Preparation of N-(2,4-dimethoxyphenyl)-3,8-dimethyl-5-isopropyl-1-azulene sulfonamide (4b)

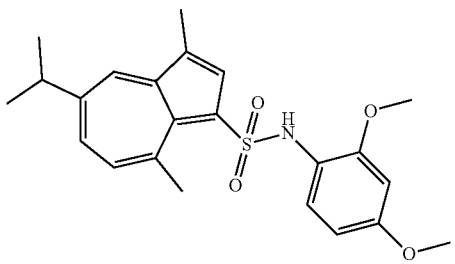

4b

The process steps of this example are as follows:

25 ml round-bottom flask was added with azulene sodium sulphonate (1 mmol), and then under ice bath added with 10 ml of $CH_2Cl_2$, 3-5 drops of DMF and 0.5 ml of pyridine. A dropping funnel was added with a small amount of $CH_2Cl_2$ and then added with $(COCl)_2$ (2.5 mmol), which was then slowly dropwise added into the round-bottom flask. After completion of the reaction, a mixture solution of 2 ml of $Et_3N$, 1 ml of pyridine and 2,4-dimethoxy aniline (1.5 mmol) was slowly dropwise added into the reaction solution through a dropping funnel. After completion of dropwise addition, the mixture was reacted at room temperature for 1 h, and then added with an equal volume of water into the flask, and added with dilute hydrochloric acid to adjust pH to 5-6, extracted with $CH_2Cl_2$, and the organic layer was dried over anhydrous $Na_2SO_4$, then concentrated by rotary evaporation, and the resultant crude product was purified through column chromatography to obtain N-(2,4-dimethoxyphenyl)-3,8-dimethyl-5-isopropyl-1-azulene sulfonamide (purple crystals). Yield: 27%. m.p. 114-116° C. $^1$H NMR (400 MHz, CDCl$_3$) δ (ppm): 1.36 (d, J=6.8 Hz, 6H), 2.50 (s, 3H), 3.10 (q, J=6.4 Hz, J=6.4 Hz, 1H), 3.42 (s, 3H), 3.72 (s, 6H, OCH$_3$), 6.31-6.37 (m, 2H, PhH), 7.00 (s, 1H, PhH), 7.37 (d, J=10.8 Hz, 1H), 7.56 (d, J=11.2 Hz, 1H), 8.02 (s, 1H), 8.22 (d, J=2.0 Hz, 1H); IR (KBr) v: 3349, 2963, 2843, 1511, 1458, 1369, 1145, 895, 834; HRMS (ESI) m/z calcd for $C_{23}H_{27}NO_4S$ [M+H]$^+$ 414.1733. found 414.1746.

Example 3

Preparation of N,5-diisopropyl-3,8-dimethyl-1-azulene sulfonamide (4c)

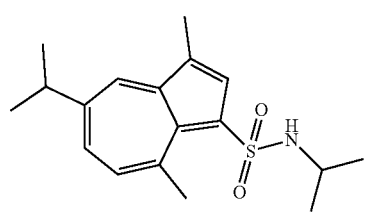

4c

The process steps of this example are as follows:

25 ml round-bottom flask was added with azulene sodium sulphonate (1 mmol), and then under ice bath added with 10 ml of $CH_2Cl_2$, 3-5 drops of DMF and 0.5 ml of pyridine. A dropping funnel was added with a small amount of $CH_2Cl_2$ and then added with $(COCl)_2$ (2.5 mmol), which was then slowly dropwise added into the round-bottom flask. After completion of the reaction, a mixture solution of 2 ml of $Et_3N$, 1 ml of pyridine and isopropyl amine (1.5 mmol) was slowly dropwise added into the reaction solution through a dropping funnel. After completion of dropwise addition, the mixture was reacted at room temperature for 1 h, and then added with an equal volume of water into the flask, and added with dilute hydrochloric acid to adjust pH to 5-6, extracted with $CH_2Cl_2$, and the organic layer was dried over anhydrous $Na_2SO_4$, then concentrated by rotary evaporation, and the resultant crude product was purified through column chromatography to obtain N,5-diisopropyl-3,8-dimethyl-1-azulene sulfonamide (purple crystals). Yield: 34%. m.p. 128-130° C. $^1$H NMR (400 MHz, CDCl$_3$) δ (ppm): 1.15 (d, J=7 Hz, 6H, CH$_3$), 1.38 (d, J=7.2 Hz, 6H), 2.58 (s, 3H), 3.12 (q, J=6.8 Hz, J=6.8 Hz, 1H), 3.37 (s, 3H), 3.53 (m, 1H, CH), 7.37 (d, J=11.2 Hz, 1H), 7.57 (d, J=11.2 Hz, 1H), 8.16 (s, 1H), 8.26 (d, J=2.0 Hz, 1H); IR (KBr) v: 3274, 2967, 2866, 1368, 1133; HRMS (ESI) m/z calcd for $C_{18}H_{25}NO_2S$ [M+H]$^+$ 320.1679. found 320.1693.

Example 4

Preparation of N-(1-naphthyl)-3,8-dimethyl-5-isopropyl-1-azulene sulfonamide (4d)

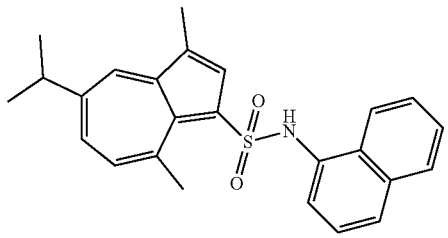

4d

The process steps of this example are as follows:

25 ml round-bottom flask was added with azulene sodium sulphonate (1 mmol), and then under ice bath added with 10 ml of $CH_2Cl_2$, 3-5 drops of DMF and 0.5 ml of pyridine. A dropping funnel was added with a small amount of $CH_2Cl_2$ and then added with $(COCl)_2$ (2.5 mmol), which was then slowly dropwise added into the round-bottom flask. After completion of the reaction, a mixture solution of 2 ml of $Et_3N$, 1 ml of pyridine and naphthylamine (1.5 mmol) was slowly dropwise added into the reaction solution through a dropping funnel. After completion of dropwise addition, the mixture was reacted at room temperature for 1 h, and then added with an equal volume of water into the flask, and added with dilute hydrochloric acid to adjust pH to 5-6, extracted with $CH_2Cl_2$, and the organic layer was dried over anhydrous $Na_2SO_4$, then concentrated by rotary evaporation, and the resultant crude product was purified through column chromatography to obtain N-(1-naphthyl)-3,8-dimethyl-5-isopropyl-1-azulene sulfonamide (purple crystals). Yield: 35%. m.p. 140-142° C. $^1$H NMR (400 MHz, CDCl$_3$) δ (ppm): 1.37 (d, J=7.6 Hz, 6H), 2.49 (s, 3H), 3.12 (q, J=7.2 Hz, J=7.2 Hz, 1H), 3.45 (s, 3H), 7.17-7.60 (m, 5H, PhH), 7.39 (d, J=11.2 Hz, 1H), 7.58 (d, J=10.8 Hz, 1H), 7.82 (d, J=8.0 Hz, 1H), 8.01 (d, J=8.0 Hz, 1H), 8.08 (s, 1H), 8.26 (d, J=2.0 Hz, 1H); IR (Mk) v: 3253, 2957, 2867, 1460, 1369, 1139, 773; HRMS (ESI) m/z calcd for $C_{25}H_{25}NO_2S$ [M+H]$^+$ 404.1679. found 404.1691.

Example 5

Preparation of N-isobutyl-3,8-dimethyl-5-isopropyl-1-azulene sulfonamide (4e)

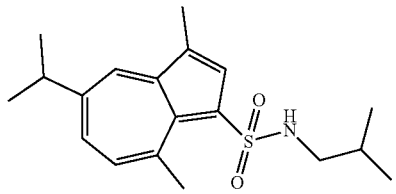

4e

The process steps of this example are as follows:

25 ml round-bottom flask was added with azulene sodium sulphonate (1 mmol), and then under ice bath added with 10 ml of $CH_2Cl_2$, 3-5 drops of DMF and 0.5 ml of pyridine. A dropping funnel was added with a small amount of $CH_2Cl_2$ and then added with $(COCl)_2$ (2.5 mmol), which was then slowly dropwise added into the round-bottom flask. After completion of the reaction, a mixture solution of 2 ml of $Et_3N$, 1 ml of pyridine and isobutylamine (1.5 mmol) was slowly dropwise added into the reaction solution through a dropping funnel. After completion of dropwise addition, the mixture reacted at room temperature for 1 h, and then added with an equal volume of water into the flask, and added with dilute hydrochloric acid to adjust pH to 5-6, extracted with $CH_2Cl_2$, and the organic layer was dried over anhydrous $Na_2SO_4$, then concentrated by rotary evaporation, and the resultant crude product was purified through column chromatography to obtain N-isobutyl-3,8-dimethyl-5-isopropyl-1-azulene sulfonamide (purple crystals). Yield: 20%. m.p. 117-118° C. $^1$H NMR (400 MHz, CDCl$_3$) δ (ppm): 0.90 (d, J=6.8 Hz, 6H, CH$_3$), 1.38 (d, J=6.8 Hz, 6H), 1.79 (m, 1H, CH), 2.58 (s, 3H), 2.89 (t, J=6.4 Hz, 2H, CH$_2$), 3.12 (q, J=7.2 Hz, J=7.2 Hz, 1H), 3.37 (s, 3H), 7.37 (d, J=10.4 Hz, 1H), 7.57 (d, J=11.2 Hz, 1H), 8.07 (s, 1H), 8.27 (s, 1H); IR (KBr) v: 3316, 2955, 2865, 1461, 1370, 1149; HRMS (ESI) m/z calcd for $C_{19}H_{27}NO_2S$ [M+H]$^+$ 334.1835. found 334.1910.

Example 6

Preparation of N-propyl-3,8-dimethyl-5-isopropyl-1-azulene sulfonamide (4f)

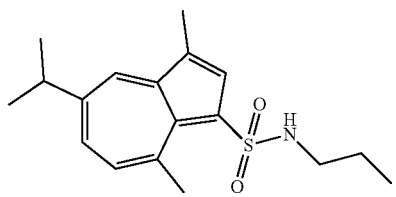

4f

The process steps of this example are as follows:

25 ml round-bottom flask was added with azulene sodium sulphonate (1 mmol), and then under ice bath added with 10 ml of $CH_2Cl_2$, 3-5 drops of DMF and 0.5 ml of pyridine. A dropping funnel was added with a small amount of $CH_2Cl_2$ and then added with $(COCl)_2$ (2.5 mmol), which was then slowly dropwise added into the round-bottom flask. After completion of the reaction, a mixture solution of 2 ml of $Et_3N$, 1 ml of pyridine and n-propylamine (1.5 mmol) was slowly dropwise added into the reaction solution through a dropping funnel. After completion of dropwise addition, the mixture was reacted at room temperature for 1 h, and then added with an equal volume of water into the flask, and added with dilute hydrochloric acid to adjust pH to 5-6, extracted with $CH_2Cl_2$, and the organic layer was dried over anhydrous $Na_2SO_4$, then concentrated by rotary evaporation, and the resultant crude product was purified through column chromatography to obtain N-propyl-3,8-dimethyl-5-isopropyl-1-azulene sulfonamide (purple powder). Yield: 31%. m.p. 60-62° C. $^1$H NMR (400 MHz, CDCl$_3$) δ (ppm): 0.90 (t, J=7.2 Hz, 3H, CH$_3$), 1.38 (d, J=6.8 Hz, 6H), 1.56 (m, 2H, CH$_2$), 2.57 (s, 3H), 3.06 (m, 2H, CH$_2$), 3.12 (q, J=7.2 Hz, J=7.2 Hz, 1H), 3.36 (s, 3H), 7.37 (d, J=11.2 Hz, 1H), 7.57 (d, J=11.2 Hz, 1H), 8.08 (s, 1H), 8.26 (s, 1H); IR (KBr) v: 3304, 2960, 2870, 1369, 1150; HRMS (ESI) m/z calcd for $C_{18}H_{25}NO_2S$ [M+H]$^+$ 320.1688. found 320.1687.

Example 7

Preparation of N-(4-methylphenyl)-3,8-dimethyl-5-isopropyl-1-azulene sulfonamide (4g)

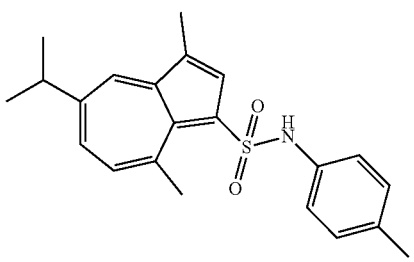

4g

The process steps of this example are as follows:

25 ml round-bottom flask was added with azulene sodium sulphonate (1 mmol), and then under ice bath added with 10 ml of $CH_2Cl_2$, 3-5 drops of DMF and 0.5 ml of pyridine. A dropping funnel was added with a small amount of $CH_2Cl_2$ and then added with $(COCl)_2$ (2.5 mmol), which was then slowly dropwise added into the round-bottom flask. After completion of the reaction, a mixture solution of 2 ml of $Et_3N$, 1 ml of pyridine and p-toluidine (1.5 mmol) was slowly dropwise added into the reaction solution through a dropping funnel. After completion of dropwise addition, the mixture was reacted at room temperature for 1 h, and then added with an equal volume of water into the flask, and added with dilute hydrochloric acid to adjust pH to 5-6, extracted with $CH_2Cl_2$, and the organic layer was dried over anhydrous $Na_2SO_4$, then concentrated by rotary evaporation, and the resultant crude product was purified through column chromatography to obtain N-(4-methylphenyl)-3,8-dimethyl-5-isopropyl-1-azulene sulfonamide (purple powder). Yield: 33%. m.p. 146-148° C. $^1$H NMR (400 MHz, CDCl$_3$) δ (ppm): 1.37 (d, J=6.8 Hz, 6H), 2.23 (s, 3H, PhCH$_3$), 2.51 (s, 3H), 3.12 (q, J=7.2 Hz, J=7.2 Hz, 1H), 3.41 (s, 3H), 6.94 (d, J=8.4 Hz, 2H, PhH), 7.00

(d, J=8.4 Hz, 2H, PhH), 7.38 (d, J=11.2 Hz, 1H), 7.57 (d, J=11.2 Hz, 1H), 8.06 (s, 1H), 8.25 (d, J=2.0 Hz, 1H); IR (KBr) v: 3315, 2959, 2864, 1514, 1465, 1368, 1155, 811; HRMS (ESI) m/z calcd for $C_{22}H_{25}NO_2S$ [M+H]$^+$ 368.1678. found 368.1693.

Example 8

Preparation of N-ethyl-3,8-dimethyl-5-isopropyl-1-azulene sulfonamide (4h)

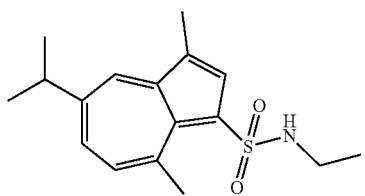

4h

The process steps of this example are as follows:

25 ml round-bottom flask was added with azulene sodium sulphonate (1 mmol), and then under ice bath added with 10 ml of $CH_2Cl_2$, 3-5 drops of DMF and 0.5 ml of pyridine. A dropping funnel was added with a small amount of $CH_2Cl_2$ and then added with $(COCl)_2$ (2.5 mmol), which was then slowly dropwise added into the round-bottom flask. After completion of the reaction, a mixture solution of 2 ml of $Et_3N$, 1 ml of pyridine and ethylamine (1.5 mmol) was slowly dropwise added into the reaction solution through a dropping funnel. After completion of dropwise addition, the mixture was reacted at room temperature for 1 h, and then added with an equal volume of water into the flask, and added with dilute hydrochloric acid to adjust pH to 5-6, extracted with $CH_2Cl_2$, and the organic layer was dried over anhydrous $Na_2SO_4$, then concentrated by rotary evaporation, and the resultant crude product was purified through column chromatography to obtain N-ethyl-3,8-dimethyl-5-isopropyl-1-azulene sulfonamide (blue floccule). Yield: 35%. m.p. 96-98° C. $^1$H NMR (400 MHz, CDCl$_3$) δ (ppm): 1.17 (t, J=7.2 Hz, 3H, CH$_3$), 1.37 (d, J=6.8 Hz, 6H), 2.58 (s, 3H), 3.09 (m, 2H, CH$_2$), 3.16 (q, J=7.2 Hz, J=7.2 Hz, 1H), 3.37 (s, 3H), 7.37 (d, J=10.8 Hz, 1H), 7.58 (d, J=11.2 Hz, 1H), 8.09 (s, 1H), 8.27 (d, J=2.0 Hz, 1H); IR (KBr) v: 3314, 2965, 1365, 1153; HRMS (ESI) m/z calcd for $C_{17}H_{23}NO_2S$ [M+H]$^+$ 306.1522. found 306.1526.

Example 9

Preparation of N-cyclohexyl-3,8-dimethyl-5-isopropyl-1-azulene sulfonamide (4i)

4i

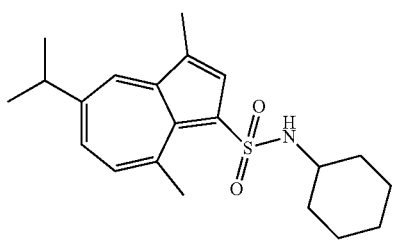

The process steps of this example are as follows:

25 ml round-bottom flask was added with azulene sodium sulphonate (1 mmol), and then under ice bath added with 10 ml of $CH_2Cl_2$, 3-5 drops of DMF and 0.5 ml of pyridine. A dropping funnel was added with a small amount of $CH_2Cl_2$ and then added with $(COCl)_2$ (2.5 mmol), which was then slowly dropwise added into the round-bottom flask. After completion of the reaction, a mixture solution of 2 ml of $Et_3N$, 1 ml of pyridine and cyclohexylamine (1.5 mmol) was slowly dropwise added into the reaction solution through a dropping funnel. After completion of dropwise addition, the mixture was reacted at room temperature for 1 h, and then added with an equal volume of water into the flask, and added with dilute hydrochloric acid to adjust pH to 5-6, extracted with $CH_2Cl_2$, and the organic layer was dried over anhydrous $Na_2SO_4$, then concentrated by rotary evaporation, and the resultant crude product was purified through column chromatography to obtain N-cyclohexyl-3,8-dimethyl-5-isopropyl-1-azulene sulfonamide (purple floccule). Yield: 42%. m.p. 108-109° C. $^1$H NMR (400 MHz, CDCl$_3$) δ (ppm): 1.38 (d, J=7.2 Hz, 6H), 1.91-1.50 (m, 10H), 2.58 (s, 3H), 3.12 (q, J=7.2 Hz, J=7.2 Hz, 1H), 3.27 (m, 1H, CH), 3.37 (s, 3H), 7.36 (d, J=10.4 Hz, 1H), 7.57 (d, J=10.4 Hz, 1H), 8.15 (s, 1H), 8.26 (d, J=2.0 Hz, 1H); IR (KBr) v: 3323, 2924, 2852, 1367, 1140; HRMS (ESI) m/z calcd for $C_{21}H_{29}NO_2S$ [M+H]$^+$ 360.1992. found 360.1992.

Example 10

Preparation of N-benzyl-3,8-dimethyl-5-isopropyl-1-azulene sulfonamide (4j)

4j

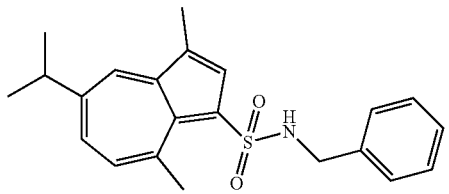

The process steps of this example are as follows:

25 ml round-bottom flask was added with azulene sodium sulphonate (1 mmol), and then under ice bath added with 10 ml of $CH_2Cl_2$, 3-5 drops of DMF and 0.5 ml of pyridine. A dropping funnel was added with a small amount of $CH_2Cl_2$ and then added with $(COCl)_2$ (2.5 mmol), which was then slowly dropwise added into the round-bottom flask. After completion of the reaction, a mixture solution of 2 ml of $Et_3N$, 1 ml of pyridine and benzylamine (1.5 mmol) was slowly dropwise added into the reaction solution through a dropping funnel. After completion of dropwise addition, the mixture was reacted at room temperature for 1 h, and then added with an equal volume of water into the flask, and added with dilute hydrochloric acid to adjust pH to 5-6, extracted with $CH_2Cl_2$, and the organic layer was dried over anhydrous $Na_2SO_4$, then concentrated by rotary evaporation, and the resultant crude product was purified through column chromatography to obtain N-benzyl-3,8-dimethyl-5-isopropyl-1-azulene sulfonamide (dark blue floccule). Yield: 48%. m.p. 124-126° C. m.p. 124-126° C. $^1$H NMR (400 MHz, CDCl$_3$) δ (ppm): 1.39 (d, J=6.8 Hz, 6H), 2.58 (s, 3H), 3.14 (q, J=7.2 Hz, J=7.2 Hz, 1H), 3.37 (s, 3H), 4.23 (d, J=6.0 Hz, 2H, CH$_2$), 7.22-7.24 (m, 5H, PhH), 7.38 (d, J=10.8 Hz, 1H), 7.57 (d, J=10.8 Hz, 1H), 8.13 (s, 1H), 8.28 (d, J=2.0 Hz, 1H); IR (KBr) v: 3327, 2958, 2863, 1542, 1366, 1147; HRMS (ESI) m/z calcd for $C_{22}H_{25}NO_2S$ [M+H]$^+$ 368.1679. found 368.1683.

Example 11

Preparation of N-(4-chlorophenyl)-3,8-dimethyl-5-isopropyl-1-azulene sulfonamide (4k)

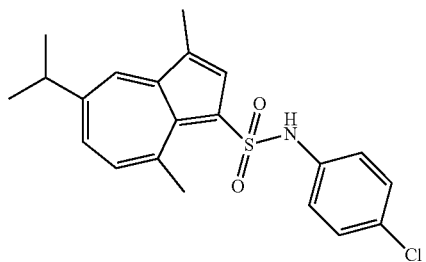

4k

The process steps of this example are as follows:

A 25 ml round-bottom flask was added with azulene sodium sulphonate (1 mmol), and then under ice bath added with 10 ml of $CH_2Cl_2$, 3-5 drops of DMF and 0.5 ml of pyridine. A dropping funnel was added with a small amount of $CH_2Cl_2$ and then added with $(COCl)_2$ (2.5 mmol), which was then slowly dropwise added into the round-bottom flask. After completion of the reaction, a mixture solution of 2 ml of $Et_3N$, 1 ml of pyridine and p-chloroaniline (1.5 mmol) was slowly dropwise added into the reaction solution through a dropping funnel. After completion of dropwise addition, the mixture was reacted at room temperature for 1 h, and then added with an equal volume of water into the flask, and added with dilute hydrochloric acid to adjust pH to 5-6, extracted with $CH_2Cl_2$, and the organic layer was dried over anhydrous $Na_2SO_4$, then concentrated by rotary evaporation, and the resultant crude product was purified through column chromatography to obtain N-(4-chlorophenyl)-3,8-dimethyl-5-isopropyl-1-azulene sulfonamide (purple powder). Yield: 22%. m.p. 134-135° C. $^1$H NMR (400 MHz, CDCl$_3$) δ (ppm): 1.37 (d, J=6.8 Hz, 6H), 2.51 (s, 3H), 3.13 (q, J=7.2 Hz, J=7.2 Hz, 1H), 3.39 (s, 3H), 6.99 (d, J=8 Hz, 2H, PhH), 7.15 (d, J=8 Hz, 2H, PhH), 7.40 (d, J=11.2 Hz, 1H), 7.61 (d, J=10.8 Hz, 1H), 8.02 (s, 1H), 8.27 (d, J=2.0 Hz, 1H); IR (KBr) v: 3298, 2957, 2862, 1492, 1369, 1137, 820, 691; HRMS (ESI) m/z calcd for $C_{21}H_{22}ClNO_2S$ [M+H]$^+$ 388.1132. found 388.1145.

Example 12

Preparation of N-(4-aminophenyl)-3,8-dimethyl-5-isopropyl-1-azulene sulfonamide (4l)

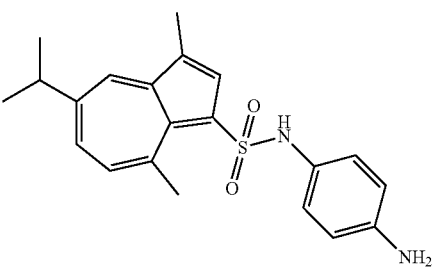

4l

The process steps of this example are as follows:
25 ml round-bottom flask was added with azulene sodium sulphonate (1 mmol), and then under ice bath added with 10 ml of $CH_2Cl_2$, 3-5 drops of DMF and 0.5 ml of pyridine. A dropping funnel was added with a small amount of $CH_2Cl_2$ and then added with $(COCl)_2$ (2.5 mmol), which was then slowly dropwise added into the round-bottom flask. After completion of the reaction, a mixture solution of 2 ml of $Et_3N$, 1 ml of pyridine and p-phenylenediamine (1.5 mmol) was slowly dropwise added into the reaction solution through a dropping funnel. After completion of dropwise addition, the mixture was reacted at room temperature for 1 h, and then added with an equal volume of water into the flask, and added with dilute hydrochloric acid to adjust pH to 5-6, extracted with $CH_2Cl_2$, and the organic layer was dried over anhydrous $Na_2SO_4$, then concentrated by rotary evaporation, and the resultant crude product was purified through column chromatography to obtain N-(4-aminophenyl)-3,8-dimethyl-5-isopropyl-1-azulene sulfonamide (purple crystals). Yield: 29%. m.p. 88-90° C. $^1$H NMR (400 MHz, DMSO-d$_6$) δ (ppm): 1.31 (d, J=6.4 Hz, 6H), 2.49 (s, 3H), 3.17 (q, J=6.8 Hz, J=6.8 Hz, 1H), 3.30 (s, 3H), 4.84 (s, 2H, NH$_2$), 6.37 (d, J=8.0 Hz, 2H, PhH), 6.78 (d, J=8.0 Hz, 2H, PhH), 7.44 (d, J=10.8 Hz, 1H), 7.73 (d, J=10.4 Hz, 1H), 7.92 (s, 1H), 8.30 (s, 1H); IR (KBr) v: 3374, 3301, 2958, 2864, 1624, 1513, 1371, 1146, 824; HRMS (ESI) m/z calcd for $C_{21}H_{24}N_2O_2S$ [M+H]$^+$ 369.1631. found 369.1641.

Example 13

Preparation of N-amino-3,8-dimethyl-5-isopropyl-1-azulene sulfonamide (4m)

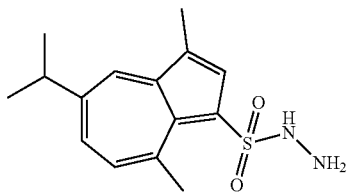

4m

The process steps of this example are as follows:
25 ml round-bottom flask was added with azulene sodium sulphonate (1 mmol), and then under ice bath added with 10 ml of $CH_2Cl_2$, 3-5 drops of DMF and 0.5 ml of pyridine. A dropping funnel was added with a small amount of $CH_2Cl_2$ and then added with $(COCl)_2$ (2.5 mmol), which was then slowly dropwise added into the round-bottom flask. After completion of the reaction, a mixture solution of 2 ml of $Et_3N$, 1 ml of pyridine and hydrazine hydrate (1.5 mmol) was slowly dropwise added into the reaction solution through a dropping funnel. After completion of dropwise addition, the mixture reacted at room temperature for 1 h, and then added with an equal volume of water into the flask, and added with dilute hydrochloric acid to adjust pH to 5-6, extracted with $CH_2Cl_2$, and the organic layer was dried over anhydrous $Na_2SO_4$, then concentrated by rotary evaporation, and the resultant crude product was purified through column chromatography to obtain N-amino-3,8-dimethyl-5-isopropyl-1-azulene sulfonamide (purple crystals).

The purified compound 4m deteriorated soon in the air and had a very poor stability, so the structural characterization and subsequent trials were not performed.

Example 14

Preparation of N-2-(indol-3-methyl)-2-methoxy-formyl methylene-3',8'-dimethyl-5'-isopropyl azulene-1'-sulfonamide (5d)

The structure formula is shown as follows:

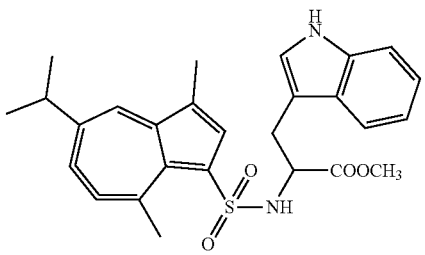 [SMILES: COC(=O)C(Cc1c[nH]c2ccccc12)NS(=O)(=O)C1=C2C(C)=C=C=C(C(C)C)C=C2C(C)=C1]

The process steps of this example are as follows:

(1) Preparation of 3,8-dimethyl-5-isopropyl azulene-1-sodium sulphonate

Under ice bath, 25 ml pear-shaped flask was sequentially added with 4 mmol of guaiazulene, 2 ml of $Ac_2O$, and then added with a mixture of 1 ml of concentrated $H_2SO_4$ and 2 ml of $Ac_2O$ through constant pressure dropping funnel (with a drying tube on the top). After completion of dropwise addition, the mixture was stirred at room temperature for about 2 h and the reaction was tracked with TLC until the raw material disappears. The mixture solution was poured into 4 ml of water, and then dropwise added with NaOH solution to adjust pH to 8-9. Then the mixture solution was cooled to precipitate, leached, and washed with cold water and petroleum ether sequentially, dried, to obtain 1.05 g of blue solid. Yield: 87.5%. m.p. 106-107° C.

(2) Preparation of L-Tryptophan Methyl Ester Hydrochloride

Under ice bath, 100 ml round-bottom flask was added with 60 ml of methanol, and then slowly added with 4 ml of $SOCl_2$ through constant pressure dropping funnel (with a drying tube on the top), and NaOH solution was used to absorb exhaust. After stirring for 1 h, 8 mmol of L-tryptophan (3d) was added and stirred at room temperature for 30 min, and then refluxed at 66° C. for 6 h. The reaction was tracked by TLC until the raw material disappears, with a solution of 2% ninhydrin in ethanol as chromogenic reagent. The solvent was evaporated out to obtain L-tryptophan methyl ester hydrochloride. Yield: 100%.

(3) Preparation of N-2-(indol-3-methyl)-2-methoxy-formyl methylene-3',8'-dimethyl-5'-isopropyl azulene-1'-sulfonamide (5d)

Under ice bath, 25 ml pear-shaped flask was sequentially added with 2 mmol of azulene sodium sulphonate, 0.8 ml of DMF, and 5 ml of $CH_2Cl_2$, 0.8 ml of Py, then added with a mixture of 5 mmol of $(COCl)_2$ and 2.5 ml of $CH_2Cl_2$ through constant pressure dropping funnel (with a drying tube on the top). The produced acyl chloride was tested using n-propylamine. The reaction was tracked by TLC until the raw material disappears. Then the mixture was added with 2.5 mmol of L-tryptophan methyl ester hydrochloride, and slowly dropwise added with 3 ml of $Et_3N$ and 1 ml of Py through constant pressure dropping funnel. After completion of dropwise addition, the mixture was stirred at room temperature over night. The reaction solution was poured into a small beaker containing 15 ml of water, and added with an appropriate amount of dilute HCl to neutralize excessive $Et_3N$ and Py and adjust pH to 5-6, then extracted with $CH_2Cl_2$ for three times. The organic layers were combined and evaporated to remove the solvent. The residue was purified by column chromatography on silica gel (silica gel: 300-400 mesh; petroleum ether-ethyl acetate (V:V=4:1) as eluent) to obtain N-2-(indol-3-methyl)-2-methoxyformyl methylene-3',8'-dimethyl-5'-isopropyl azulene-1'-sulfonamide (5d), purple crystals. Yield: 20%. m.p. 178-180° C. $^1$H NMR (CDCl$_3$, 400 MHz) δ: 8.19 (s, 1H), 7.99 (s, 2H), 7.52 (d, J=11.6 Hz, 1H), 7.38 (d, J=7.9 Hz, 1H), 7.25 (d, J=4.7 Hz, 1H), 7.23 (d, J=8.1 Hz, 1H), 7.09 (t, J=7.2 Hz, 8.1 Hz, 1H), 6.98 (dd, J=4.4 Hz, 8.4 Hz, 2H), 5.28 (d, J=8.9 Hz, 1H), 4.32~4.27, 3.30~3.26 (m, 3H), 3.51 (s, 3H), 3.21 (s, 3H), 3.19~3.08 (m, 1H), 2.47 (s, 3H), 1.37 (d, J=6.9 Hz, 6H). IR (KBr) v: 3304 (NH), 1744 (C=O), 1370 (as, S=O), 1145 (s, S=O) cm$^{-1}$. HRMS (ESI) calcd for $C_{27}H_{30}N_2O_4S$ [M+H]$^+$ 479.1999 found 479.1990; [M+Na]$^+$ 501.1818 found 501.1837; [M+K]$^+$ 517.1558 found 517.1551.

Example 15

Preparation of N-3-methoxyformylethyl-3',8'-dimethyl-5'-isopropyl azulene-1'-sulfonamide (5h)

The structure formula is shown as follows:

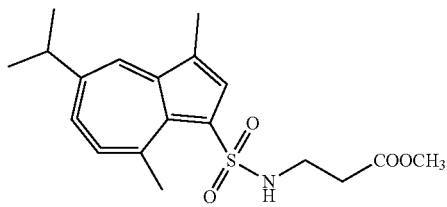 [SMILES: COC(=O)CCNS(=O)(=O)C1=C2C(C)=C=C=C(C(C)C)C=C2C(C)=C1]

The process steps of this example are as follows:

(1) Preparation of 3,8-dimethyl-5-isopropyl azulene-1-sodium sulphonate

Under ice bath, 25 ml pear-shaped flask was sequentially added with 4 mmol of guaiazulene, 2 ml of $Ac_2O$, and then added with a mixture of 1 ml of concentrated $H_2SO_4$ and 2 ml of $Ac_2O$ through constant pressure dropping funnel (with a drying tube on the top). After completion of dropwise addition, the mixture was stirred at room temperature for about 2 h and the reaction was tracked with TLC until the raw material disappears. The mixture solution was poured into 4 ml of water, and then dropwise added with NaOH solution to adjust pH to 8-9. Then the mixture solution was cooled to precipitate, leached, and washed with cold water and petroleum ether sequentially, dried, to obtain 1.05 g of blue solid. Yield: 87.5%. m.p. 106-107° C.

(2) Preparation of β-alanine methyl ester methyl ester hydrochloride

Under ice bath, 100 ml round-bottom flask was added with 60 ml of methanol, and then slowly added with 4 ml of $SOCl_2$ through constant pressure dropping funnel (with a drying tube on the top), and NaOH solution was used to absorb exhaust. After stirring for 1 h, 8 mmol of β-alanine was added and stirred at room temperature for 30 min, and then refluxed at 66° C. for 6 h. The reaction was tracked by TLC until the raw material disappears, with a solution of 2% ninhydrin in ethanol as chromogenic reagent. The solvent was evaporated out to obtain β-alanine methyl ester hydrochloride. Yield: 100%.

(3) Preparation of N-3-methoxyformylethyl-3',8'-dimethyl-5'-isopropyl azulene-1'-sulfonamide (5h)

Under ice bath, 25 ml pear-shaped flask was sequentially added with 2 mmol of azulene sodium sulphonate, 0.8 ml of DMF, and 5 ml of $CH_2Cl_2$, 0.8 ml of Py, then added with a mixture of 5 mmol of $(COCl)_2$ and 2.5 ml of $CH_2Cl_2$ through constant pressure dropping funnel (with a drying tube on the top). The produced acyl chloride was tested using n-propylamine. The reaction was tracked by TLC until the raw material disappears. Then the mixture was added with 2.5 mmol of β-alanine methyl ester hydrochloride, and slowly dropwise added with 3 ml of $Et_3N$ and 1 ml of Py through constant pressure dropping funnel. After completion of dropwise addition, the mixture was stirred at room temperature over night. The reaction solution was poured into a small beaker containing 15 ml of water, and added with an appropriate amount of dilute HCl to neutralize excessive $Et_3N$ and Py and adjust pH to 5-6, then extracted with $CH_2Cl_2$ for three times. The organic layers were combined and evaporated to remove the solvent. The residue was purified by column chromatography on silica gel (silica gel: 300-400 mesh; petroleum ether-ethyl acetate (V:V=4:1) as eluent) to obtain N-3-methoxyformyl-ethyl-3',8'-dimethyl-5'-isopropyl azulene-1'-sulfonamide (5h), purple crystals. Yield: 23%. m.p. 94-96° C. $^1$H NMR ($CDCl_3$, 400 MHz) δ: 8.27 (s, 1H), 8.10 (s, 1H), 7.58 (d, J=11.8 Hz, 1H), 7.37 (d, J=11.0 Hz, 1H), 5.28 (t, J=8.4 Hz, 7.5 Hz, 1H), 3.65 (s, 3H), 3.36 (s, 3H), 3.30 (dd, J=6.3 Hz, 6.1 Hz, 2H), 3.16-3.09 (m, 1H), 2.59-2.56 (m, 2H), 2.58 (s, 3H), 1.37 (d, J=6.8 Hz, 6H). IR (KBr) v: 3314 (NH), 1728 (C=O), 1370 (as, S=O), 1154 (s, S=O) $cm^{-1}$. HRMS (ESI) calcd for $C_{19}H_{25}NO_4S$ $[M+H]^+$ 364.1577 found 364.1583; $[M+Na]^+$ 386.1397 found 386.1405; $[M+K]^+$ 402.1136 found 402.1151.

Example 16

Preparation of N-2-(2-methylpropyl)-2-carboxymethylene-3',8'-dimethyl-5'-isopropyl azulene-1'-sulfonamide (6b)

The structure formula is shown as follows:

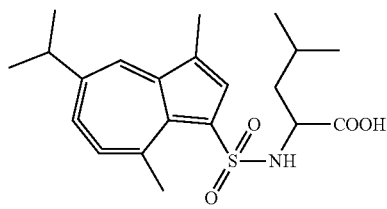 [SMILES: CC1=C=C=C(C(C)C)C=C2C(C)=CC(S(=O)(=O)NC(CC(C)C)C(=O)O)=C12]

The process steps of this example are as follows:

(1) Preparation of 3,8-dimethyl-5-isopropyl azulene-1-sodium sulphonate

Under ice bath, 25 ml pear-shaped flask was sequentially added with 4 mmol of guaiazulene, 2 ml of $Ac_2O$, and then added with a mixture of 1 ml of concentrated $H_2SO_4$ and 2 ml of $Ac_2O$ through constant pressure dropping funnel (with a drying tube on the top). After completion of dropwise addition, the mixture was stirred at room temperature for about 2 h and the reaction was tracked with TLC until the raw material disappears. The mixture solution was poured into 4 ml of water, and then dropwise added with NaOH solution to adjust pH to 8-9. Then the mixture solution was cooled to precipitate, leached, and washed with cold water and petroleum ether sequentially, dried, to obtain 1.05 g of blue solid. Yield: 87.5%. m.p. 106-107° C.

(2) Preparation of L-leucine methyl ester methyl ester hydrochloride

Under ice bath, 100 ml round-bottom flask was added with 60 ml of methanol, and then slowly added with 4 ml of $SOCl_2$ through constant pressure dropping funnel (with a drying tube on the top), and NaOH solution was used to absorb exhaust. After stirring for 1 h, 8 mmol of L-leucine was added and stirred at room temperature for 30 min, and then refluxed at 66° C. for 6 h. The reaction was tracked by TLC until the raw material disappears, with a solution of 2% ninhydrin in ethanol as chromogenic reagent. The solvent was evaporated out to obtain L-leucine methyl ester hydrochloride. Yield: 100%.

(3) Preparation of N-2-(2-methylpropyl)-2-methoxyformyl methylene-3',8'-dimethyl-5'-isopropyl azulene-1'-sulfonamide Under ice bath, 25 ml pear-shaped flask was sequentially added with 2 mmol of azulene sodium sulphonate, 0.8 ml of DMF, and 5 ml of $CH_2Cl_2$, 0.8 ml of Py, then added with a mixture of 5 mmol of $(COCl)_2$ and 2.5 ml of $CH_2Cl_2$ through constant pressure dropping funnel (with a drying tube on the top). The produced acyl chloride was tested using n-propylamine. The reaction was tracked by TLC until the raw material disappears. Then the mixture was added with 2.5 mmol of L-leucine methyl ester hydrochloride, and slowly dropwise added with 3 ml of $Et_3N$ and 1 ml of Py through constant pressure dropping funnel. After completion of dropwise addition, the mixture was stirred at room temperature over night. The reaction solution was poured into a small beaker containing 15 ml of water, and added with an appropriate amount of dilute HCl to neutralize excessive $Et_3N$ and Py and adjust pH to 5-6, then extracted with $CH_2Cl_2$ for three times. The organic layers were combined and evaporated to remove the solvent. The residue was purified by column chromatography on silica gel (silica gel: 300-400 mesh; eluent: petroleum ether-ethyl acetate (V:V=4:1)) to obtain N-2-(2-methylpropyl)-2-methoxyformyl methylene-3',8'-dimethyl-5'-isopropyl azulene-1'-sulfonamide (5b), purple crystals. Yield: 21%. m.p. 68-70° C. $^1$H NMR ($CDCl_3$, 400 MHz) δ: 8.26 (s, 1H), 8.14 (s, 1H), 7.58 (d, J=11.2 Hz, 1H), 7.39 (d, J=11.2 Hz, 1H), 5.13 (d, J=10.0 Hz, 1H), 3.97-3.90 (m, 1H), 3.43 (s, 3H), 3.38 (s, 3H), 3.13 (dd, J=7.1 Hz, 6.8 Hz, 1H), 2.56 (s, 3H), 1.74-1.67 (m, 1H), 1.50-1.40 ((m, 2H), 1.37 (d, J=6.8 Hz, 6H), 0.84 (d, J=6.6 Hz, 3H), 0.69 (d, J=6.6 Hz, 3H). IR (KBr) v: 3308 (NH), 1746 (C=O), 1370 (as, S=O), 1155 (s, S=O) $cm^{-1}$. HRMS (ESI) calcd for $C_{22}H_{31}NO_4S$ $[M+H]^+$ 406.2047 found 406.2048; $[M+K]^+$ 444.1605 found 444.1652.

(4) Preparation of N-2-(2-methylpropyl)-2-carboxymethylene-3',8'-dimethyl-5'-isopropyl azulene-1'-sulfonamide (6b)

1 mmol of N-2-(2-methylpropyl)-2-methoxyformylmeth-ylene-3',8'-dimethyl-5'-isopropyl azulene-1'-sulfonamide (5b) was dissolved in 5 ml of methanol and 15 ml of water, and added with 0.8 ml of 5% NaOH solution, and extracted with CH$_2$Cl$_2$ for three times. The aqueous layers were retained, added with dilute HCl until reaching pH 5-6, then extracted with CH$_2$Cl$_2$ for three times. The organic layers were combined, evaporated to remove the solvent. The residue was purified by column chromatography on silica gel (silica gel: 300-400 mesh; Eluent: petroleum ether-ethyl acetate (V:V=4:1)) to obtain N-2-(2-methylpropyl)-2-carboxymethylene-3',8'-dimethyl-5'-isopropyl azulene-1'-sulfonamide (6b), purple crystals. Yield: 95%. m.p. 44-46° C. $^1$H NMR (DMSO-d$_6$, 400 MHz) δ: 10.80 (s, 1H), 10.52 (s, 1H), 10.39 (d, J=9.4 Hz, 1H), 10.22 (d, J=10.9 Hz, 1H), 9.93 (d, J=11.4 Hz, 1H), 6.13~6.07 (m, 1H), 5.79 (s, 3H), 5.71~5.64 (m, 1H), 5.03 (s, 3H), 4.14~3.99 (m, 2H), 3.87~3.84 (m, 1H), 3.82 (d, J=6.9 Hz, 6H), 3.28 (d, J=6.4 Hz, 3H), 3.06 (d, J=6.4 Hz, 3H). IR (KBr) v: 3329 (NH), 1726 (C=O), 1372 (as, S=O), 1151 (s, S=O) HRMS (ESI) calcd for C$_{21}$H$_{29}$NO$_4$S [M+H]$^+$ 392.1890 found 392.1898; [M+Na]$^+$ 414.1710 found 414.1723; [M+K]$^+$ 430.1449 found 430.1467.

Example 17

Preparation of N-2-(indol-3-methyl)-2-carboxymethylene-3',8'-dimethyl-5'-isopropyl azulene-1'-sulfonamide (6c)

The structure formula is shown as follows:

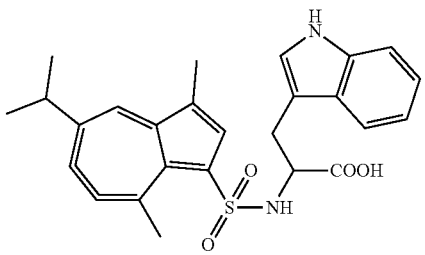 [SMILES: CC1=C=C=C(C(C)C)C=C2C(C)=CC(S(=O)(=O)NC(Cc3c[nH]c4ccccc34)C(=O)O)=C12]

(1) Preparation of 3,8-dimethyl-5-isopropyl azulene-1-sodium sulphonate (2)

Under ice bath, 25 ml pear-shaped flask was sequentially added with 4 mmol of guaiazulene, 2 ml of Ac$_2$O, and then added with a mixture of 1 ml of concentrated H$_2$SO$_4$ and 2 ml of Ac$_2$O through constant pressure dropping funnel (with a drying tube on the top). After completion of dropwise addition, the mixture was stirred at room temperature for about 2 h and the reaction was tracked with TLC until the raw material disappears. The mixture solution was poured into 4 ml of water, and then dropwise added with NaOH solution to adjust pH to 8-9. Then the mixture solution was cooled to precipitate, leached, and washed with cold water and petroleum ether sequentially, dried, to obtain 1.05 g of blue solid. Yield: 87.5%. m.p. 106-107° C.

(2) Preparation of L-tryptophan methyl ester hydrochloride

Under ice bath, 100 ml round-bottom flask was added with 60 ml of methanol, and then slowly added with 4 ml of SOCl$_2$ through constant pressure dropping funnel (with a drying tube on the top), and NaOH solution was used to absorb exhaust. After stirring for 1 h, 8 mmol of L-tryptophan was added and stirred at room temperature for 30 min, and then refluxed at 66° C. for 6 h. The reaction was tracked by TLC until the raw material disappears, with a solution of 2% ninhydrin in ethanol as chromogenic reagent. The solvent was evaporated out to obtain L-tryptophan methyl ester hydrochloride. Yield: 100%.

(3) Preparation of N-2-(indol-3-methyl)-2-methoxyformyl methylene-3',8'-dimethyl-5'-isopropyl azulene-1'-sulfonamide (5d)

Under ice bath, 25 ml pear-shaped flask was sequentially added with 2 mmol of azulene sodium sulphonate, 0.8 ml of DMF, and 5 ml of CH$_2$Cl$_2$, 0.8 ml of Py, then added with a mixture of 5 mmol of (COCl)$_2$ and 2.5 ml of CH$_2$Cl$_2$ through constant pressure dropping funnel (with a drying tube on the top). The produced acyl chloride was tested using n-propylamine. The reaction was tracked by TLC until the raw material disappears. Then the mixture was added with 2.5 mmol L-tryptophan methyl ester hydrochloride, and slowly dropwise added with 3 ml of Et$_3$N and 1 ml of Py through constant pressure dropping funnel. After completion of dropwise addition, the mixture was stirred at room temperature over night. The reaction solution was poured into a small beaker containing 15 ml of water, and added with an appropriate amount of dilute HCl to neutralize excessive Et$_3$N and Py and adjust pH to 5-6, then extracted with CH$_2$Cl$_2$ for three times. The organic layers were combined and evaporated to remove the solvent. The residue was purified by column chromatography on silica gel (silica gel: 300-400 mesh; petroleum ether-ethyl acetate (V:V=4:1) as eluent) to obtain N-2-(indol-3-methyl)-2-methoxyformyl methylene-3',8'-dimethyl-5'-isopropyl azulene-1'-sulfonamide (5d), purple crystals. Yield: 20%. m.p. 178-180° C. $^1$H NMR (CDCl$_3$, 400 MHz) δ: 8.19 (s, 1H), 7.99 (s, 2H), 7.52 (d, J=11.6 Hz, 1H), 7.38 (d, J=7.9 Hz, 1H), 7.25 (d, J=4.7 Hz, 1H), 7.23 (d, J=8.1 Hz, 1H), 7.09 (t, J=7.2 Hz, 8.1 Hz, 1H), 6.98 (dd, J=4.4 Hz, 8.4 Hz, 2H), 5.28 (d, J=8.9 Hz, 1H), 4.32~4.27, 3.30~3.26 (m, 3H), 3.51 (s, 3H), 3.21 (s, 3H), 3.19~3.08 (m, 1H), 2.47 (s, 3H), 1.37 (d, J=6.9 Hz, 6H). IR (KBr) v: 3304 (NH), 1744 (C=O), 1370 (as, S=O), 1145 (s, S=O) cm$^{-1}$. HRMS (ESI) calcd for C$_{27}$H$_{30}$N$_2$O$_4$S [M+H]$^+$ 479.1999 found 479.1990; [M+Na]$^+$ 501.1818 found 501.1837; [M+K]$^+$ 517.1558 found 517.1551.

(4) Preparation of N-2-(indol-3-methyl)-2-carboxymethylene-3',8'-dimethyl-5'-isopropyl azulene-1'-sulfonamide (6c)

1 mmol of N-2-(indol-3-methyl)-2-methoxyformyl methylene-3',8'-dimethyl-5'-isopropyl azulene-1'-sulfonamide (5d) was dissolved in 5 ml of methanol and 15 ml of water, and added with 0.8 ml of 5% NaOH solution, and extracted with CH$_2$Cl$_2$ for three times. The aqueous layers were retained, added with dilute HCl until reaching pH 5-6, then extracted with CH$_2$Cl$_2$ for three times. The organic layers were combined, evaporated to remove the solvent. The residue was purified by column chromatography on silica gel (silica gel: 300-400 mesh; eluent: petroleum ether-ethyl acetate (V:V=4:1)) to obtain N-2-(indol-3-methyl)-2-carboxymethylene-3',8'-dimethyl-5'-isopropyl azulene-1'-sulfonamide (6c), purple crystals. Yield: 98%. m.p. 107-108° C. $^1$H NMR (DMSO-d$_6$, 400 MHz) δ: 13.35 (s, 1H), 10.69 (s, 1H), 10.52 (d, J=8.4 Hz, 1H), 10.00 (s, 1H), 9.81 (dd, J=11.2 Hz, 8.1 Hz, 2H), 9.74 (d, J=7.9 Hz, 1H), 9.68 (s, 1H), 9.50 (t, J=7.4 Hz, 7.6 Hz, 1H), 9.36 (t, J=7.6 Hz, 1H), 6.43~6.37 (m, 1H), 5.66 (s, 3H), 5.61 (dd, J=6.4 Hz, 6.1 Hz, 2H), 5.51 (dd, J=8.4 Hz, 8.3 Hz, 1H), 5.00 (s, 3H), 3.81 (d, J=7.0 Hz, 6H). IR (KBr) v: 3409 (NH), 1736 (C=O), 1378 (as, S=O), 1146 (s, S=O) cm$^{-1}$. HRMS (ESI) calcd for $C_{26}H_{28}N_2O_4S$ [M+H]$^+$ 465.1843 found 465.1841; [M+Na]$^+$ 487.1662 found 487.1672; [M+K]$^+$ 503.1401 found 503.1414.

Example 18

Preparation of N-(2-carbonyl-2-(2-(2-thienylmethylene)ethyl)-3',8'-dimethyl-5'-isopropyl azulene-1'-sulfonamide (8a)

The structure formula is shown as follows:

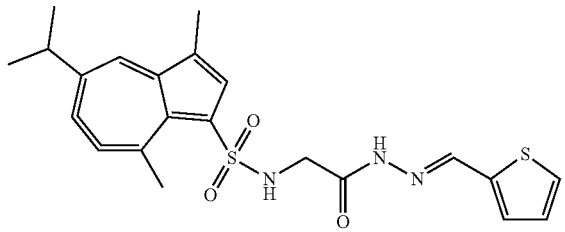 [SMILES: CC1=C=C=C(C(C)C)C=C2C(C)=CC(S(=O)(=O)NCC(=O)N/N=C/c3cccs3)=C12]

(1) Preparation of 3,8-dimethyl-5-isopropyl azulene-1-sodium sulphonate

Under ice bath, 25 ml pear-shaped flask was sequentially added with 4 mmol of guaiazulene, 2 ml of Ac$_2$O, and then added with a mixture of 1 ml of concentrated H$_2$SO$_4$ and 2 ml of Ac$_2$O through constant pressure dropping funnel (with a drying tube on the top). After completion of dropwise addition, the mixture was stirred at room temperature for about 2 h and the reaction was tracked with TLC until the raw material disappears. The mixture solution was poured into 4 ml of water, and then dropwise added with NaOH solution to adjust pH to 8-9. Then the mixture solution was cooled to precipitate, leached, and washed with cold water and petroleum ether sequentially, dried, to obtain 1.05 g of blue solid. Yield: 87.5%. m.p. 106-107° C.

(2) Preparation of glycine methyl ester hydrochloride

Under ice bath, 100 ml round-bottom flask was added with 60 ml of methanol, and then slowly added with 4 ml of SOCl$_2$ through constant pressure dropping funnel (with a drying tube on the top), and NaOH solution was used to absorb exhaust. After stirring for 1 h, 8 mmol of glycine was added and stirred at room temperature for 30 min, and then refluxed at 66° C. for 6 h. The reaction was tracked by TLC until the raw materials disappeared, with a solution of 2% ninhydrin in ethanol as chromogenic reagent. The solvent was evaporated out to obtain glycine methyl ester hydrochloride. Yield: 100%.

(3) Preparation of N-methoxyformylmethyl-3',8'-dimethyl-5'-isopropyl azulene-1'-sulfonamide (5a)

Under ice bath, 25 ml pear-shaped flask was sequentially added with 2 mmol of azulene sodium sulphonate, 0.8 ml of DMF, and 5 ml of CH$_2$Cl$_2$, 0.8 ml of Py, then added with a mixture of 5 mmol of (COCl)$_2$ and 2.5 ml of CH$_2$Cl$_2$ through constant pressure dropping funnel (with a drying tube on the top). The produced acyl chloride was tested using n-propylamine. The reaction was tracked by TLC until the raw material disappears. Then the mixture was added with 2.5 mmol of glycine methyl ester hydrochloride, and slowly dropwise added with 3 ml of Et$_3$N and 1 ml of Py through constant pressure dropping funnel. After completion of dropwise addition, the mixture was stirred at room temperature over night. The reaction solution was poured into a small beaker containing 15 ml of water, and added with an appropriate amount of dilute HCl to neutralize excessive Et$_3$N and Py and adjust pH to 5-6, then extracted with CH$_2$Cl$_2$ for three times. The organic layers were combined and evaporated to remove the solvent. The residue was purified by column chromatography on silica gel (silica gel: 300-400 mesh; eluent: petroleum ether-ethyl acetate (V:V=4:1)) to obtain N-methoxyformylmethyl-3',8'-dimethyl-5'-isopropyl azulene-1'-sulfonamide (5a), purple crystals. Yield: 28%. m.p. 70-72° C. $^1$H NMR (CDCl$_3$, 400 MHz) δ: 8.28 (s, 1H), 8.11 (s, 1H), 7.59 (d, J=11.0 Hz, 1H), 7.39 (d, J=11.4 Hz, 1H), 5.17 (t, J=10.3 Hz, 1H), 3.84 (d, J=5.3 Hz, 2H), 3.67 (s, 3H), 3.38 (s, 3H), 3.13 (dd, J=6.9 Hz, 6.9 Hz, 1H), 2.57 (s, 3H), 1.38 (d, J=7.0 Hz, 6H). IR (KBr) v: 3315 (NH), 1735 (C=O), 1370 (as, S=O), 1155 (s, S=O) cm$^{-1}$. HRMS (ESI) calcd for $C_{18}H_{23}NO_4S$ [M+H]$^+$ 350.1421 found 350.1429; [M+Na]$^+$ 372.1240 found 372.1226; [M+K]$^+$ 388.0979 found 388.0989.

(4) Preparation of N-(2-hydrazo-2-oxoethyl)-3',8'-dimethyl-5'-isopropyl azulene-1'-sulfonamide (7a)

1 mmol of N-methoxyformylmethyl-3',8'-dimethyl-5'-isopropyl azulene-1'-sulfonamide (5a), 60 ml of anhydrous ethanol, 3 mmol of 80% hydrazine hydrate were sequencially added into 100 ml bottom flask, and reacted under reflux at 80° C. for about 8 h. The reaction was tracked by TLC until the raw material disappears. The reaction solution was evaporated to remove the solvent and the residue was purified by column chromatography on silica gel (silica gel: 300-400 mesh; Eluent: petroleum ether-ethyl acetate-ethanol (V:V:V=4:1:0.5)) to obtain N-(2-hydrazo-2-oxoethyl)-3',8'-dimethyl-5'-isopropyl azulene-1'-sulfonamide (7a), purple crystals. Yield: 80.5%. m.p. 71-73° C. $^1$H NMR (CDCl$_3$, 400 MHz) δ: 8.28 (s, 1H), 8.02 (s, 1H), 7.61 (d, J=11.40 Hz, 1H), 7.56~7.52 (m, 1H), 7.39 (d, J=10.9 Hz, 1H), 5.68~5.60 (m, 1H), 3.40 (t, J=4.32 Hz, 3.61 Hz, 1H), 3.33 (s, 3H), 2.56 (s, 3H), 3.13 (dd, J=6.92 Hz, 2H), 2.04~1.96 (m, 2H), 1.38 (d, J=6.93 Hz, 6H). IR (KBr) v: 3281 (NH$_2$), 1660 (C=O), 1543 (C—N), 1375 (as, S=O), 1253 (s, S=O) cm$^{-1}$. HRMS (ESI) calcd for $C_{17}H_{23}N_3O_3S$ [M−H]$^-$ 348.1382 found 348.1392.

(5) Preparation of N-(2-carbonyl-2-(2-(2-thienylmethylene)ethyl)-3',8'-dimethyl-5'-isopropyl azulene-1'-sulfonamide (8a)

0.5 mmol of N-(2-hydrazo-2-oxoethyl)-3',8'-dimethyl-5'-isopropyl azulene-1'-sulfonamide (7a), 15 ml of anhydrous ethanol, 0.6 mmol of 2-thiophene formaldehyde were added into 25 ml pear-shaped flask and stirred at 35° C. overnight. The reaction was tracked by TLC until the raw material disappears. The reaction solution was evaporated to remove the solvent and the residue was purified by column chromatography on silica gel (silica gel: 300-400 mesh; eluent: petroleum ether-ethyl acetate-ethanol (V:V:V=4:1:0.5)) to obtain N-(2-carbonyl-2-(2-(2-thienylmethylene)ethyl)-3',8'-dimethyl-5'-isopropyl azulene-1'-sulfonamide (8a), purple crystals. Yield: 78%. m.p. 69-70° C. $^1$H NMR (CDCl$_3$, 400 MHz) δ: 9.66 (s, 1H), 8.25 (d, J=2.10 Hz, 1H), 8.13 (s, 1H), 7.90 (s, 1H), 7.56 (d, J=11.32 Hz, 1H), 7.40~7.34 (d, J=3.27 Hz, 2H), 7.24 (d, J=3.63 Hz, 1H), 7.03 (dd, J=3.55 Hz, 3.55 Hz, 1H), 5.67 (t, J=4.34 Hz, 4.77 Hz, 1H), 4.27 (d, J=4.86 Hz, 2H), 3.41 (s, 3H), 3.11 (dd, J=7.22 Hz, 7.02 Hz, 1H), 2.56 (s, 3H), 1.36 (d, J=6.89 Hz, 6H). IR (KBr) v: 3396 (NH), 1685 (C=O), 1546 (C=N), 1381 (as, S=O), 1153 (s, S=O) cm$^{-1}$. HRMS (ESI) calcd for $C_{22}H_{25}N_3O_3S_2$ [M–H]$^-$ 442.1259 found 442.1250.

The advantages of the derivatives of the present invention will be illustrated by the following experimental examples.

Experimental Example 1

Stability Studies

1. Experimental Drugs
  Test Drugs:
  (1) N-substituted isopropyldimethyl azulene sulfonamide derivatives prepared according to examples 1 to 18: 4a-4l
  4a: N-(3-bromophenyl)-3,8-dimethyl-5-isopropyl-1-azulene sulfonamide (prepared in example 1)
  4b: N-(2,4-dimethoxyphenyl)-3,8-dimethyl-5-isopropyl-1-azulene sulfonamide (prepared in example 2)
  4c: N,5-diisopropyl-3,8-dimethyl-1-azulene sulfonamide (prepared in example 3)
  4d: N-(1-naphthyl)-3,8-dimethyl-5-isopropyl-1-azulene sulfonamide (prepared in example 4)
  4e: N-isobutyl-3,8-dimethyl-5-isopropyl-1-azulene sulfonamide (prepared in example 5)
  4f: N-propyl-3,8-dimethyl-5-isopropyl-1-azulene sulfonamide (prepared in example 6)
  4g: N-(4-methylphenyl)-3,8-dimethyl-5-isopropyl-1-azulene sulfonamide (prepared in example 7)
  4h: N-ethyl-3,8-dimethyl-5-isopropyl-1-azulene sulfonamide (prepared in example 8)
  4i: N-cyclohexyl-3,8-dimethyl-5-isopropyl-1-azulene sulfonamide (prepared in example 9)
  4j: N-benzyl-3,8-dimethyl-5-isopropyl-1-azulene sulfonamide (prepared in example 10)
  4k: N-(4-chlorophenyl)-3,8-dimethyl-5-isopropyl-1-azulene sulfonamide (prepared in example 11)
  4l: N-(4-aminophenyl)-3,8-dimethyl-5-isopropyl-1-azulene sulfonamide (prepared in example 12)

2. High-Temperature Test

The test samples were open-stored in culture dishes at 60° C. for 10 days, and taken and detected on Day 5 and Day 10.

The characteristics, especially colour change were observed.

Melting points were measured by automatic melting point apparatus.

By self-reflection, TLC is used to observe whether the spot numbers were increased after 5 days and 10 days.

TABLE 1

High-temperature test (60° C.)

| Test sample | Appearance | | | Melting point (° C.) | | | Spot numbers on TLC | | |
|---|---|---|---|---|---|---|---|---|---|
| | Day 0 | Day 5 | Day 10 | Day 0 | Day 5 | Day 10 | Day 0 | Day 5 | Day 10 |
| Azulene sulfonate sodium | dark blue flake crystals | blue flake crystals | light blue powder | 104.0-106.0 | 102.5-104.0 | 98.5-100.0 | 1 | 2 | 4 |
| 4a | purple crystals | purple crystals | purple crystals | 172.5-174.0 | 172.0-173.5 | 172.5-174.0 | 1 | 1 | 1 |
| 4b | purple crystals | purple crystals | purple crystals | 114.0-115.5 | 114.5-116.0 | 113.5-115.0 | 1 | 1 | 1 |
| 4c | purple crystals | purple crystals | purple crystals | 127.5-130.0 | 127.5-129.5 | 127.5-129.5 | 1 | 1 | 1 |
| 4d | purple crystals | purple crystals | purple crystals | 140.0-142.5 | 141.5-142.5 | 140.0-142.5 | 1 | 1 | 1 |
| 4e | purple powder | purple powder | purple powder | 117.0-118.0 | 117.5-118.5 | 117.5-118.5 | 1 | 1 | 1 |
| 4f | purple powder | purple powder | purple powder | 59.5-62.5 | 60.0-62.0 | 60.0-62.0 | 1 | 1 | 1 |
| 4g | purple floccule | purple floccule | purple floccule | 146.0-148.5 | 146.0-148.0 | 145.5-147.5 | 1 | 1 | 1 |
| 4h | blue floccule | blue floccule | blue floccule | 123.5-125.5 | 123.5-125.5 | 124.5-125.0 | 1 | 1 | 1 |
| 4i | purple floccule | purple floccule | purple floccule | 107.5-108.5 | 107.0-108.5 | 107.0-108.5 | 1 | 1 | 1 |
| 4j | dark blue floccule | dark blue floccule | blue floccule | 124.0-125.5 | 124.0-125.5 | 124.0-125.5 | 1 | 1 | 1 |
| 4k | purple powder | purple powder | purple powder | 134.5-135.0 | 134.0-135.5 | 134.0-135.5 | 1 | 1 | 1 |
| 4l | purple crystals | purple crystals | purple crystals | 87.5-89.0 | 88.0-89.0 | 88.0-89.0 | 1 | 1 | 1 |

3. High Humidity Test

The test samples were open-stored in closed constant humidity desiccators under the condition of 25° C. and relative humidity of 90%+5% for 10 days, and taken and detected on Day 5 and Day 10. Meanwhile, each sample was accurately weighed before and after test.

The characteristics, especially colour change was observed.

Melting points were measured by an automatic melting point apparatus.

By self-reflection, TLC is used to observe whether the spot numbers were increased after 5 days and 10 days.

TABLE 2

High humidity test (90% ± 5%)

Obervation Items

| Test sample | Appearance | | | Melting point (° C.) | | | Spot numbers on TLC | | | hygroscopic rate (%) | |
|---|---|---|---|---|---|---|---|---|---|---|---|
| | Day 0 | Day 5 | Day 10 | Day 0 | Day 5 | Day 10 | Day 0 | Day 5 | Day 10 | Day 0 | Day 5 |
| Azulene sulfonate sodium | dark blue flake crystal | blue flake crystals | light blue powder | 104.0-106.0 | 100.5-105.5 | 98.5-102.0 | 1 | 3 | 3 | 2.16% | 3.69% |
| 4a | purple crystals | purple crystals | purple crystals | 172.5-174.0 | 172.0-174.5 | 172.0-174.5 | 1 | 1 | 1 | 1.01% | 1.46% |
| 4b | purple crystals | purple crystals | purple crystals | 114.0-115.5 | 114.0-115.5 | 114.0-115.5 | 1 | 1 | 1 | 0.97% | 1.24% |
| 4c | purple crystals | purple crystals | purple crystals | 127.5-130.0 | 128.0-130.5 | 128.0-130.5 | 1 | 1 | 1 | 0.95% | 1.32% |
| 4d | purple crystals | purple crystals | purple crystals | 140.0-142.5 | 140.0-142.5 | 140.0-142.5 | 1 | 1 | 1 | 1.23% | 1.61% |
| 4e | purple powder | purple powder | purple powder | 117.0-118.0 | 116.5-118.5 | 116.5-118.5 | 1 | 1 | 1 | 1.07% | 1.51% |
| 4f | purple powder | purple powder | purple powder | 59.5-62.5 | 59.5-63.0 | 59.5-63.0 | 1 | 1 | 1 | 1.13% | 1.28% |
| 4g | purple floccule | purple floccule | purple floccule | 146.0-148.5 | 145.5-148.5 | 145.5-148.5 | 1 | 1 | 1 | 1.56% | 2.01% |
| 4h | blue floccule | blue floccule | blue floccule | 123.5-125.5 | 123.5-125.5 | 123.5-125.5 | 1 | 1 | 1 | 1.14% | 2.11% |
| 4i | purple floccule | purple floccule | purple floccule | 108.5-109.0 | 108.5-109.5 | 107.5-108.5 | 1 | 1 | 1 | 1.89% | 2.35% |
| 4j | dark blue floccule | dark blue floccule | blue floccule | 124.0-126.0 | 124.0-126.5 | 124.5-126.5 | 1 | 1 | 1 | 1.24% | 2.08% |
| 4k | purple powder | purple powder | purple powder | 134.5-135.0 | 134.5-135.5 | 134.5-135.5 | 1 | 1 | 1 | 1.17% | 1.87% |
| 4l | purple crystals | purple crystals | purple crystals | 87.5-89.0 | 87.5-89.5 | 87.5-89.5 | 1 | 1 | 1 | 1.09% | 1.81% |

4. Intense Light Irradiation Test

The test samples were open-stored in "adjustable light boxes" under the conditions of illumination of 4500LX±500LX for 10 days, and taken and detected on Day 5 and Day 10 with regards to dry items.

The characteristics, especially colour change was observed.

Melting points were measured by an automatic melting point apparatus.

By self-reflection, TLC is used to observe whether the spot numbers were increased after 5 days and 10 days.

TABLE 3

Intense light irradiation test (4500LX ± 500LX)

Obervation Items

| Test sample | Appearance | | | Melting point (° C.) | | | Spot numbers on TLC | | |
|---|---|---|---|---|---|---|---|---|---|
| | Day 0 | Day 5 | Day 10 | Day 0 | Day 5 | Day 10 | Day 0 | Day 5 | Day 10 |
| Azulene sulfonate sodium | dark blue flake crystals | blue flake crystals | light blue powder | 104.0-106.0 | 102.5-105.5 | 98.54-103.5 | 1 | 3 | >4 |
| 4a | purple crystals | purple crystals | purple crystals | 172.5-174.0 | 172.0-175.0 | 173.0-174.0 | 1 | 1 | 1 |
| 4b | purple crystals | purple crystals | purple crystals | 114.0-11.5 | 114.0-11.5 | 114.0-11.5 | 1 | 1 | 1 |
| 4c | purple crystals | purple crystals | purple crystals | 127.5-130.0 | 127.0-129.5 | 125.0-126.5 | 1 | 1 | 2 |
| 4d | purple crystals | purple crystals | purple crystals | 140.0-142.5 | 141.5-143.0 | 140.0-142.0 | 1 | 1 | 1 |
| 4e | purple powder | purple powder | purple powder | 117.0-118.0 | 117.5-118.0 | 115.0-117.5 | 1 | 1 | 2 |
| 4f | purple powder | purple powder | purple powder | 59.5-62.5 | 58.5-62.0 | 57.5-61.5 | 1 | 1 | 2 |

TABLE 3-continued

| | Intense light irradiation test (4500LX ± 500LX) | | | | | | | | |
|---|---|---|---|---|---|---|---|---|---|
| | Obervation Items | | | | | | | | |
| | Appearance | | | Melting point (° C.) | | | Spot numbers on TLC | | |
| Test sample | Day 0 | Day 5 | Day 10 | Day 0 | Day 5 | Day 10 | Day 0 | Day 5 | Day 10 |
| 4g | purple floccule | purple floccule | purple floccule | 146.0-148.5 | 145.0-147.5 | 143.5-147.5 | 1 | 1 | 2 |
| 4h | blue floccule | blue floccule | blue floccule | 123.5-125.5 | 122.0-125.5 | 121.0-126.0 | 1 | 1 | 2 |
| 4i | purple floccule | purple floccule | purple floccule | 107.5-108.5 | 107.5-108.5 | 170.0-108.5 | 1 | 1 | 1 |
| 4j | dark blue floccule | dark blue floccule | blue floccule | 124.0-125.5 | 123.5-125.5 | 122..0-126.5 | 1 | 1 | 2 |
| 4k | purple powder | purple powder | purple powder | 134.5-135.0 | 134.0-135.5 | 134.0-135.5 | 1 | 1 | 1 |
| 4l | purple crystals | purple crystals | purple crystals | 87.5-89.0 | 87.5-89.0 | 87.5-89.5 | 1 | 1 | 1 |

It can be seen from the above experiments of stability studies that the N-substituted isopropyldimethyl azulene sulfonamide derivatives such as 4a, 4b, 4c, 4d, 4e, 4f, 4g, 4h, 4i, 4j, 4k, 4l provided by the present invention have better light, humidity and heat stability than azulene sulfonate sodium and do not need special equipments or special treatment during the storage and transportation of the products, and thus reduce the product cost and increase the product safety.

Experimental Example 2

Biological Activity Tests

1. Experimental Drugs
   Test Drugs:
   (1) N-substituted isopropyldimethyl azulene sulfonamide derivatives prepared according to examples 1 to 18: 4a-4l
   4a: N-(3-bromophenyl)-3,8-dimethyl-5-isopropyl-1-azulene sulfonamide (prepared in example 1)
   4b: N-(2,4-dimethoxyphenyl)-3,8-dimethyl-5-isopropyl-1-azulene sulfonamide (prepared in example 2)
   4c: N,5-diisopropyl-3,8-dimethyl-1-azulene sulfonamide (prepared in example 3)
   4d: N-(1-naphthyl)-3,8-dimethyl-5-isopropyl-1-azulene sulfonamide (prepared in example 4)
   4e: N-isobutyl-3,8-dimethyl-5-isopropyl-1-azulene sulfonamide (prepared in example 5)
   4f: N-propyl-3,8-dimethyl-5-isopropyl-1-azulene sulfonamide (prepared in example 6)
   4g: N-(4-methylphenyl)-3,8-dimethyl-5-isopropyl-1-azulene sulfonamide (prepared in example 7)
   4h: N-ethyl-3,8-dimethyl-5-isopropyl-1-azulene sulfonamide (prepared in example 8)
   4i: N-cyclohexyl-3,8-dimethyl-5-isopropyl-1-azulene sulfonamide (prepared in example 9)
   4j: N-benzyl-3,8-dimethyl-5-isopropyl-1-azulene sulfonamide (prepared in example 10)
   4k: N-(4-chlorophenyl)-3,8-dimethyl-5-isopropyl-1-azulene sulfonamide (prepared in example 11)
   4l: N-(4-aminophenyl)-3,8-dimethyl-5-isopropyl-1-azulene sulfonamide (prepared in example 12)
   5d: N-2-(indol-3-methyl)-2-methoxyformyl methylene-3',8'-dimethyl-5'-isopropyl azulene-1'-sulfonamide (prepared in example 14)
   5h: N-3-methoxyformylethyl-3',8'-dimethyl-5'-isopropyl azulene-1'-sulfonamide (prepared in example 15)
   6b: N-2-(2-methylpropyl)-2-carboxymethylene-3',8'-dimethyl-5'-isopropyl azulene-1'-sulfonamide (prepared in example 16)
   6c: N-2-(indol-3-methyl)-2-carboxymethylene-3',8'-dimethyl-5'-isopropyl azulene-1'-sulfonamide (prepared in example 17)
   8a: N-(2-carbonyl-2-(2-(2-thienylmethylene)ethyl)-3',8'-dimethyl-5'-isopropyl azulene-1'-sulfonamide (prepared in example 18)
   (2) Guaiazulene: Jiangxi East Flavor&Fragrance Co., Ltd, China
   Omeprazole enteric-coated capsules: 20 mg/capsule, Lot: 100701, manufactured by Shangdong Laiyang Biochemistry Pharmaceutical Co. Ltd.
2. Experiment Animals
   Kunming mice, half male and half female, weighing 18-22 g, provided by the West China Animal Center
3. Experiment Instruments
   (1) Electronic balance, manufactured by Changshu Shuangjie Test Instrument Factory, model T1000, Max=1000 g, d=0.1 g, manufactured by Beijing Sartorius balance Co., Ltd, model BS210S, Max=210 g, d=0.1 mg.
4. Drug Preparation
   (1) Azulene sodium sulphonate was added with 0.5% CMC to prepare a suspension with concentration of 0.15 mg/ml.
   (2) 20 mg of Omeprazole was added with 0.5% CMC to prepare a suspension with concentration of 0.67 mg/ml.
   (3) The N-substituted isopropyldimethyl azulene sulfonamide derivatives 4a-4l prepared according to examples 1 to 12 were added with 0.5% CMC to prepare suspensions with concentration of 0.15 mg/ml.
5. Experiment Method
   Kunming mice were randomly grouped according the body weight (one model control group or negative control group, one Omeprazole control group or positive control group, one Azulene sodium sulphonate control group, twelve test drug groups), eight mice for each group, half male and half female.
   Administration: Model control group was administrated intragastrically with 0.5% CMC solution at a dose of 0.4 ml/20 g; Omeprazole control group was administrated intragastrically with Omeprazole at a dose of 0.4 ml/20 g, Azulene sodium sulphonate control group and each test drug groups were administrated intragastrically with their respective drug at a dose of 0.4 ml/20 g. The mice in each group were administrated once a day for successive five days. 0.5 hour after final administration, the mice in each group were administrated intragastrically with 0.5 ml of anhydrous ethanol, one hour later the mice were executed and dissected, and their stomaches were taken, washed and scored according to the pathological degree. For local congestion and rubefaction, score was 1; for petechial hemorrhage or erosion, score was respectively 1, for each linear erosion, score was 3. Statistical analysis was performed. Ulcer scores were calculated, significant differences between the groups were compared and the inhibition rates of ulcer were calculated [Inhibition rate of ulcer= (ulcer score of model group−ulcer score of drug administration group)/ulcer score of model group]. Experiment results are shown in Tables 4-7.

TABLE 4

Effect of target compounds on ethanol-induced gastric ulcer

| Group | Dose (mg/kg) | Number of animals | Gastri ulcer score ($\overline{X} \pm SD$) | Inhibition rate (%) |
|---|---|---|---|---|
| Model group | — | 8 | 13.00 ± 1.77 | — |
| Omeprazole | 13.4 | 8 | 6.86 ± 3.77* | 47.23 |
| Azulene sulfonate sodium | 3.0 | 8 | 7.14 ± 4.73* | 45.08 |
| 4a | 4.3 | 8 | 6.33 ± 4.50* | 51.31 |
| 4b | 4.1 | 8 | 6.14 ± 2.85* | 52.77 |
| 4d | 4.0 | 8 | 6.43 ± 2.99* | 50.54 |
| 4i | 3.6 | 8 | 6.38 ± 3.85* | 50.92 |

Compared to the model group *P<0.05. The dose of each drug was calculated according to the same molar dose of azulene sulfonate sodium.

It can be seen from the data of Table 4, among the N-substituted isopropyldimethyl azulene sulfonamide derivatives prepared according to the present invention, compounds 4a, 4b, 4d and 4i can significantly relieve the pathological degree of ethanol-induced gastric ulcer disease in mice. Their ulcer scores are significant different from that of the model group and their pharmacodynamic activities are similar to and slightly superior than that of azulene sulfonate sodium.

TABLE 5

Effect of target compounds on ethanol-induced gastric ulcer

| Group | Dose (mg/kg) | Number of animals | Ulcer score ($\overline{X} \pm SD$) | Inhibition rate (%) |
|---|---|---|---|---|
| Model group | — | 8 | 20.33 ± 12.23 | — |
| Omeprazole | 13.4 | 8 | 12.86 ± 11.89* | 36.74 |
| Azulene sulfonate sodium | 3.0 | 8 | 13.71 ± 10.75* | 32.56 |
| 4l | 3.7 | 8 | 11.14 ± 6.41* | 45.20 |

Compared to the model group *P<0.05. The dose of each drug was calculated according to the same molar dose of azulene sulfonate sodium.

It can be seen from the data of Table 5, the N-substituted isopropyldimethyl azulene sulfonamide derivative 4l prepared according to the present invention can significantly relieve the pathological degree of ethanol-induced gastric ulcer disease in mice, the ulcer score of which is significant different from that of the model group.

Meanwhile, compared to azulene sulfonate sodium, the inhibition rate of the derivative 4l increased 38%; compared to Omeprazole, the inhibition rate of the derivative 4l increased 23%. Thus, the derivative 4l has better therapeutic effect on gastric ulcer than azulene sulfonate sodium and omeprazole.

TABLE 6

Effect of target compounds on gastric ulcer activity in mice

| Group | Dose (mg/kg) | Number of animals | Gastric ulcer score ($\overline{X} \pm SD$) | Inhibition rate (%) |
|---|---|---|---|---|
| Model group | — | 8 | 17.86 ± 8.43 | — |
| Omeprazole group | 13.4 | 8 | 7.25 ± 7.15* | 59.41 |
| Azulene sulfonate sodium | 3.0 | 8 | 8.43 ± 5.74* | 52.80 |
| 5d | 4.8 | 8 | 8.71 ± 4.93* | 51.23 |
| 5h | 3.6 | 8 | 8.79 ± 4.38* | 50.78 |

Comparison of each drug group with the model group; *P<0.05.

TABLE 7

Effect of target compounds on gastric ulcer activity in mice

| Group | Dose (mg/kg) | Number of animals | Gastric ulcer score ($\overline{X} \pm SD$) | Inhibition rate (%) |
|---|---|---|---|---|
| Model group | — | 8 | 19.71 ± 7.18 | — |
| Omeprazole group | 13.4 | 8 | 8.23 ± 3.18* | 58.25 |
| 2 | 3.0 | 8 | 9.43 ± 5.74* | 52.16 |
| 6b | 3.9 | 8 | 9.67 ± 4.25* | 50.94 |
| 6c | 4.6 | 8 | 8.86 ± 4.81* | 55.05 |
| 8a | 4.4 | 8 | 10.06 ± 5.60* | 48.96 |

Comparison of each drug group with the model group; *P<0.05.

It can be seen from the data of Tables 6 and 7, most of the derivatives 5a~5h, 6a~6c, 7a~7b, 8a~8b prepared according to the present invention have certain anti-gastric ulcer activity, wherein 5d, 5h, 6b, 6c and 8a have stronger and more significant anti-gastric ulcer capability, and have significant differences compared to the model group. The experiment results show that the derivatives of guaiazulene provided by the present invention can be used to develop new drugs with stronger pharmaceutical activity for treating gastric ulcer.

To sum up, the N-substituted isopropyldimethyl azulene sulfonamide derivatives prepared according to the present invention not only improve the stability of azulene sodium sulphonate and retain the therapeutic effect on gastric ulcer disease of azulene sodium sulphonate, but also enhance the pharmaceutical activity of azulene sodium sulphonate.

INDUSTRIAL APPLICABILITY

The N-substituted isopropyldimethyl azulene sulfonamide derivatives prepared according to the present invention have significant effect on treating gastric ulcer, the activity of which is comparable with or superior than that of azulene sulfonate sodium or Omeprazole, and have excellent light, moisture, heat stability, and can reduce the product cost and enhance the product safety. Meanwhile, the preparation method of the derivatives is simple and the raw materials are readily available. Thus, the N-substituted derivatives of isopropyl dimethyl azulene sulfonamides have good prospects in industrial applications.

What is claimed is:

1. An N-substituted isopropyldimethyl azulene sulfonamide compound being:

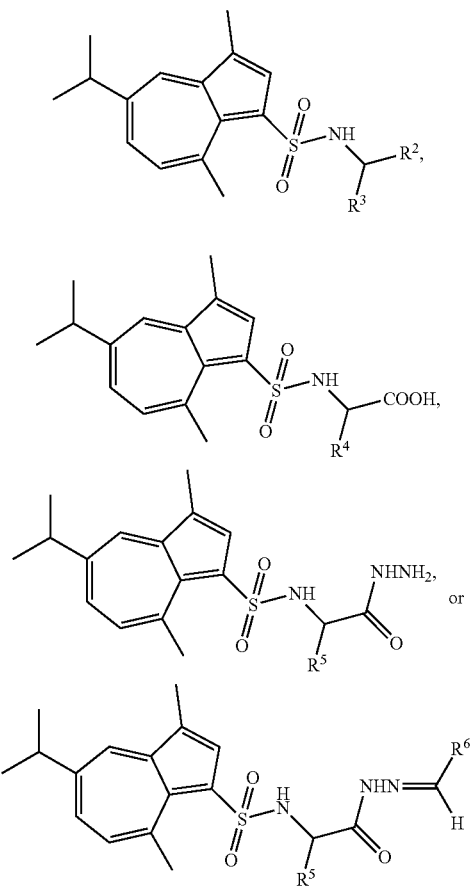

wherein $R^2$ is hydrogen or methoxycarbonyl; $R^3$ is 2 methylpropyl, phenyl, methyl, ethyl, or carbomethoxymethyl; $R^4$ is hydrogen, 2-methylpropyl, or indol-3-methyl; $R^5$ is hydrogen or indol-3-methyl; and $R^6$ is 2-thienyl.

2. An N-substituted isopropyldimethyl azulene sulfonamide compound according to claim 1, selected from the group consisting of:
   N-2-(indol-3-methyl)-2-methoxyformyl methylene-3',8'-dimethyl-5'-isopropyl azulene-1'-sulfonamide;
   N-3-methoxyformylethyl-3',8'-dimethyl-5'-isopropyl azulene-1'-sulfonamide;
   N-2-(2-methylpropyl)-2-carboxymethylene-3',8'-dimethyl-5'-isopropyl azulene-1'-sulfonamide;
   N-2-(indol-3-methyl)-2-carboxymethylene-3',8'-dimethyl-5'-isopropyl azulene-1'-sulfonamide; and
   N-(2-carbonyl-2-(2-(2-thienylmethylene)ethyl)-3',8'-dimethyl-5'-isopropyl azulene-1'-sulfonamide.

3. The N-substituted isopropyldimethyl azulene sulfonamide compound according to claim 1, wherein $R^2$ is hydrogen.

4. A method of preparing the N-substituted isopropyldimethyl azulene sulfonamide compound according to claim 3, having the structure

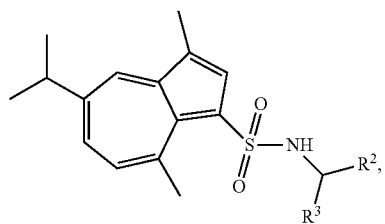

comprising the steps of:
   subjecting azulene sodium sulphonate to acetyl chlorination to generate azulene sulfonyl chloride, and
   reacting the azulene sulfonyl chloride with an amine compound to obtain

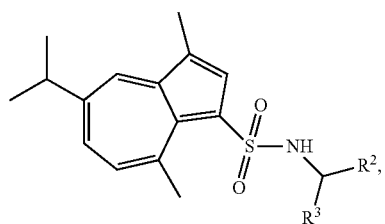

wherein said amine compound is selected from the group consisting of iso-butylamine, n-propylamine, ethylamine, β-alanine methyl ester hydrochloride, and benzylamine.

5. A method of using the N-substituted isopropyldimethyl azulene sulfonamide compound according to claim 1 for treating a digestive ulcer, the method comprising administering to a subject suffering from the digestive ulcer a pharmaceutical composition having the N-substituted isopropyldimethyl azulene sulfonamide compound as an active ingredient.

6. The method according to claim 5, wherein said digestive ulcer is a gastric ulcer.

7. A pharmaceutical composition, comprising one or more compounds according to claim 1 as active ingredients, and a pharmaceutically acceptable excipient or auxiliary component.

8. The pharmaceutical composition according to claim 7, wherein said composition is an oral or injectable composition.

9. The pharmaceutical composition according to claim 8, wherein said composition is an oral composition selected from the group consisting of tablets, pills, granules, capsules, powders, drop pills, and oral liquid.

10. A method of preparing the N-substituted isopropyldimethyl azulene sulfonamide compound according to claim 3, having the structure

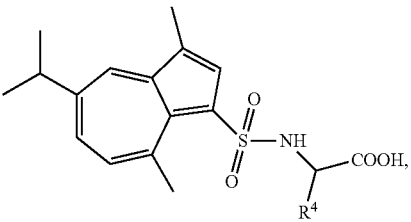

-continued

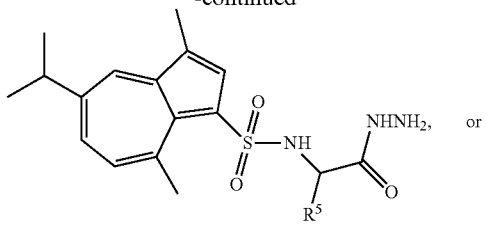NHNH₂, or

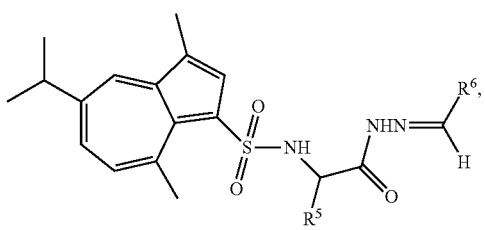

comprising the steps of:
  subjecting azulene sodium sulphonate to acetyl chlorination to generate azulene sulfonyl chloride,
  reacting the azulene sulfonyl chloride with an amine compound to form a methyl ester intermediate having the structure of

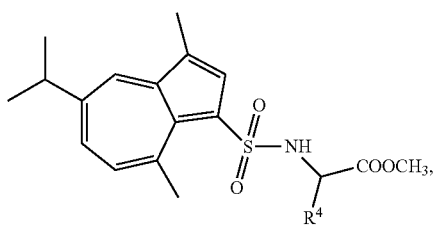

wherein said amine compound is selected from the group consisting of L-leucine methyl ester hydrochloride, L-tryptophan methyl ester hydrochloride, and glycine methyl ester hydrochloride,
  reacting said methyl ester intermediate with a sodium hydroxide solution to obtain

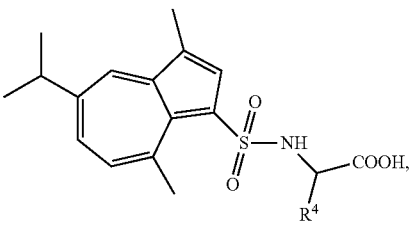

reacting said methyl ester intermediate with hydrazine hydrate to obtain

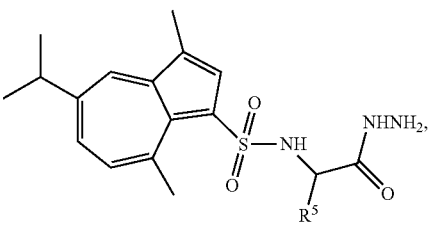

optionally reacting

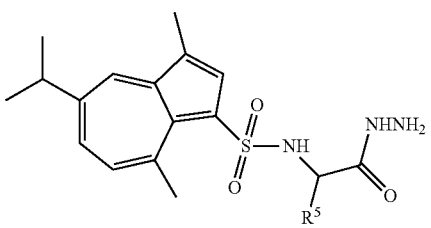

thus obtained with 2-thiophene formaldehyde to obtain

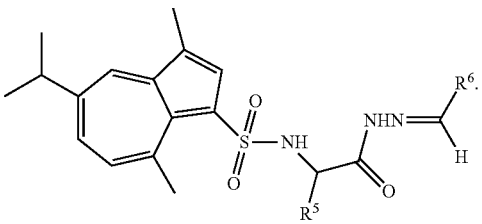

* * * * *